(12) United States Patent
Raridan, Jr.

(10) Patent No.: US 7,676,253 B2
(45) Date of Patent: Mar. 9, 2010

(54) MEDICAL SENSOR AND TECHNIQUE FOR USING THE SAME

(75) Inventor: William B. Raridan, Jr., Pleasanton, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 637 days.

(21) Appl. No.: 11/512,488

(22) Filed: Aug. 30, 2006

(65) Prior Publication Data

US 2007/0073117 A1    Mar. 29, 2007

Related U.S. Application Data

(63) Continuation of application No. 11/241,508, filed on Sep. 29, 2005.

(51) Int. Cl.
*A61B 5/1455* (2006.01)

(52) U.S. Cl. ............... 600/344; 600/310; 600/322; 600/323

(58) Field of Classification Search ......... 600/310, 600/322, 323, 344
See application file for complete search history.

(56) References Cited

U.S. PATENT DOCUMENTS

| | | | |
|---|---|---|---|
| 3,403,555 A | 10/1968 | Versaci etal. |
| 3,536,545 A | 10/1970 | Traynor et al. |
| D222,454 S | 10/1971 | Beeber |
| 3,721,813 A | 3/1973 | Condon et al. |
| 4,098,772 A | 7/1978 | Bonk et al. |
| D250,275 S | 11/1978 | Bond |
| D251,387 S | 3/1979 | Ramsay et al. |
| D262,488 S | 12/1981 | Rossman et al. |
| 4,334,544 A | 6/1982 | Hill et al. |
| 4,350,165 A | 9/1982 | Striese |
| 4,353,372 A | 10/1982 | Ayer |
| 4,380,240 A | 4/1983 | Jobsis et al. |
| 4,406,289 A | 9/1983 | Wesseling et al. |
| 4,510,551 A | 4/1985 | Brainard, II |
| 4,586,513 A | 5/1986 | Hamaguri |
| 4,603,700 A | 8/1986 | Nichols et al. |
| 4,621,643 A | 11/1986 | New, Jr. et al. |
| 4,653,498 A | 3/1987 | New, Jr. et al. |
| 4,677,528 A | 6/1987 | Miniet |

(Continued)

FOREIGN PATENT DOCUMENTS

DE    3405444    8/1985

(Continued)

OTHER PUBLICATIONS

U.S. Appl. No. 11/507,814, filed Sep. 26, 2006, Ollerdessen et al.

(Continued)

*Primary Examiner*—Eric F Winakur
*Assistant Examiner*—Etsub D Berhanu
(74) *Attorney, Agent, or Firm*—Fletcher Yoder

(57) ABSTRACT

A medical sensor may be adapted to account for factors that cause irregularities in pulse oximetry measurements or other spectrophotemetric measurements. Sensors are provided with surface features that reduce the amount of outside light or shunted light that impinge the detecting elements of the sensor. The sensor is adapted to reduce the effect of outside light or shunted light on pulse oximetry measurements.

31 Claims, 5 Drawing Sheets

U.S. PATENT DOCUMENTS

| | | | |
|---|---|---|---|
| 4,685,464 A * | 8/1987 | Goldberger et al. ......... 600/344 |
| 4,694,833 A | 9/1987 | Hamaguri |
| 4,697,593 A | 10/1987 | Evans et al. |
| 4,700,708 A | 10/1987 | New, Jr. et al. |
| 4,714,080 A | 12/1987 | Edgar, Jr. et al. |
| 4,714,341 A | 12/1987 | Hamaguri et al. |
| 4,722,120 A | 2/1988 | Lu |
| 4,726,382 A | 2/1988 | Boehmer et al. |
| 4,759,369 A | 7/1988 | Taylor |
| 4,770,179 A | 9/1988 | New, Jr. et al. |
| 4,773,422 A | 9/1988 | Isaacson et al. |
| 4,776,339 A | 10/1988 | Schreiber |
| 4,781,195 A | 11/1988 | Martin |
| 4,783,815 A | 11/1988 | Buttner |
| 4,796,636 A | 1/1989 | Branstetter et al. |
| 4,800,495 A | 1/1989 | Smith |
| 4,800,885 A | 1/1989 | Johnson |
| 4,802,486 A | 2/1989 | Goodman et al. |
| 4,805,623 A | 2/1989 | Jöbsis |
| 4,807,630 A | 2/1989 | Malinouskas |
| 4,807,631 A | 2/1989 | Hersh et al. |
| 4,819,646 A | 4/1989 | Cheung et al. |
| 4,819,752 A | 4/1989 | Zelin |
| 4,824,242 A | 4/1989 | Frick et al. |
| 4,825,872 A | 5/1989 | Tan et al. |
| 4,825,879 A | 5/1989 | Tan et al. |
| 4,830,014 A | 5/1989 | Goodman et al. |
| 4,832,484 A | 5/1989 | Aoyagi et al. |
| 4,846,183 A | 7/1989 | Martin |
| 4,848,901 A | 7/1989 | Hood, Jr. |
| 4,854,699 A | 8/1989 | Edgar, Jr. |
| 4,859,056 A | 8/1989 | Prosser et al. |
| 4,859,057 A | 8/1989 | Taylor et al. |
| 4,863,265 A | 9/1989 | Flower et al. |
| 4,865,038 A | 9/1989 | Rich et al. |
| 4,867,557 A | 9/1989 | Takatani et al. |
| 4,869,253 A | 9/1989 | Craig, Jr. et al. |
| 4,869,254 A | 9/1989 | Stone et al. |
| 4,880,304 A | 11/1989 | Jaeb et al. |
| 4,883,055 A | 11/1989 | Merrick |
| 4,883,353 A | 11/1989 | Hansmann et al. |
| 4,890,619 A | 1/1990 | Hatschek |
| 4,892,101 A | 1/1990 | Cheung et al. |
| 4,901,238 A | 2/1990 | Suzuki et al. |
| 4,908,762 A | 3/1990 | Suzuki et al. |
| 4,911,167 A | 3/1990 | Corenman et al. |
| 4,913,150 A | 4/1990 | Cheung et al. |
| 4,926,867 A | 5/1990 | Kanda et al. |
| 4,927,264 A | 5/1990 | Shiga et al. |
| 4,928,692 A | 5/1990 | Goodman et al. |
| 4,934,372 A | 6/1990 | Corenman et al. |
| 4,938,218 A | 7/1990 | Goodman et al. |
| 4,942,877 A | 7/1990 | Sakai et al. |
| 4,948,248 A | 8/1990 | Lehman |
| 4,955,379 A | 9/1990 | Hall |
| 4,960,126 A | 10/1990 | Conlon et al. |
| 4,964,408 A | 10/1990 | Hink et al. |
| 4,971,062 A | 11/1990 | Hasebe et al. |
| 4,974,591 A | 12/1990 | Awazu et al. |
| 5,007,423 A | 4/1991 | Branstetter et al. |
| 5,025,791 A | 6/1991 | Niwa |
| RE033,643 E | 7/1991 | Isaacson et al. |
| 5,028,787 A | 7/1991 | Rosenthal et al. |
| 5,035,243 A | 7/1991 | Muz |
| 5,040,039 A | 8/1991 | Schmitt et al. |
| 5,041,187 A | 8/1991 | Hink et al. |
| 5,054,488 A | 10/1991 | Muz |
| 5,055,671 A | 10/1991 | Jones |
| 5,058,588 A | 10/1991 | Kaestle |
| 5,065,749 A | 11/1991 | Hasebe et al. |
| 5,066,859 A | 11/1991 | Karkar et al. |
| 5,069,213 A | 12/1991 | Polczynski |
| 5,078,136 A | 1/1992 | Stone et al. |
| 5,086,229 A | 2/1992 | Rosenthal et al. |
| 5,088,493 A | 2/1992 | Giannini et al. |
| 5,090,410 A | 2/1992 | Saper et al. |
| 5,094,239 A | 3/1992 | Jaeb et al. |
| 5,094,240 A | 3/1992 | Muz |
| 5,099,841 A | 3/1992 | Heinonen et al. |
| 5,099,842 A | 3/1992 | Mannheimer et al. |
| H01039 H | 4/1992 | Tripp et al. |
| 5,104,623 A | 4/1992 | Miller |
| 5,109,849 A | 5/1992 | Goodman et al. |
| 5,111,817 A | 5/1992 | Clark et al. |
| 5,113,861 A | 5/1992 | Rother |
| D326,715 S | 6/1992 | Schmidt |
| 5,125,403 A | 6/1992 | Culp |
| 5,127,406 A | 7/1992 | Yamaguchi |
| 5,131,391 A | 7/1992 | Sakai et al. |
| 5,140,989 A | 8/1992 | Lewis et al. |
| 5,152,296 A | 10/1992 | Simons |
| 5,154,175 A | 10/1992 | Gunther |
| 5,158,082 A | 10/1992 | Jones |
| 5,170,786 A | 12/1992 | Thomas et al. |
| 5,188,108 A | 2/1993 | Secker et al. |
| 5,190,038 A | 3/1993 | Polson et al. |
| 5,193,542 A | 3/1993 | Missanelli et al. |
| 5,193,543 A | 3/1993 | Yelderman |
| 5,203,329 A | 4/1993 | Takatani et al. |
| 5,209,230 A | 5/1993 | Swedlow et al. |
| 5,213,099 A | 5/1993 | Tripp et al. |
| 5,216,598 A | 6/1993 | Branstetter et al. |
| 5,217,012 A | 6/1993 | Young et al. |
| 5,217,013 A | 6/1993 | Lewis et al. |
| 5,218,207 A | 6/1993 | Rosenthal |
| 5,218,962 A | 6/1993 | Mannheimer et al. |
| 5,224,478 A | 7/1993 | Sakai et al. |
| 5,226,417 A | 7/1993 | Swedlow et al. |
| 5,228,440 A | 7/1993 | Chung et al. |
| 5,237,994 A | 8/1993 | Goldberger |
| 5,239,185 A | 8/1993 | Ito et al. |
| 5,246,002 A | 9/1993 | Prosser |
| 5,246,003 A | 9/1993 | DeLonzor |
| 5,247,931 A | 9/1993 | Norwood |
| 5,247,932 A | 9/1993 | Chung et al. |
| 5,249,576 A | 10/1993 | Goldberger et al. |
| 5,253,645 A | 10/1993 | Friedman et al. |
| 5,253,646 A | 10/1993 | Delpy et al. |
| 5,259,381 A | 11/1993 | Cheung et al. |
| 5,259,761 A | 11/1993 | Schnettler et al. |
| 5,263,244 A | 11/1993 | Centa et al. |
| 5,267,562 A | 12/1993 | Ukawa et al. |
| 5,267,563 A | 12/1993 | Swedlow et al. |
| 5,267,566 A | 12/1993 | Choucair et al. |
| 5,273,036 A | 12/1993 | Kronberg et al. |
| 5,275,159 A | 1/1994 | Griebel |
| 5,278,627 A | 1/1994 | Aoyagi et al. |
| 5,279,295 A | 1/1994 | Martens et al. |
| 5,285,783 A | 2/1994 | Secker |
| 5,285,784 A | 2/1994 | Seeker |
| 5,287,853 A | 2/1994 | Vester et al. |
| 5,291,884 A | 3/1994 | Heinemann et al. |
| 5,297,548 A | 3/1994 | Pologe |
| 5,299,120 A | 3/1994 | Kaestle |
| 5,299,570 A | 4/1994 | Hatschek |
| 5,309,908 A | 5/1994 | Friedman et al. |
| 5,311,865 A | 5/1994 | Mayeux |
| 5,313,940 A | 5/1994 | Fuse et al. |
| 5,323,776 A | 6/1994 | Blakeley et al. |
| 5,329,922 A | 7/1994 | Atlee, III |
| 5,337,744 A | 8/1994 | Branigan |
| 5,339,810 A | 8/1994 | Ivers et al. |
| 5,343,818 A | 9/1994 | McCarthy et al. |
| 5,343,869 A | 9/1994 | Pross et al. |

| Patent No. | Date | Inventor(s) | Patent No. | Date | Inventor(s) |
|---|---|---|---|---|---|
| 5,348,003 A | 9/1994 | Caro | 5,555,882 A | 9/1996 | Richardson et al. |
| 5,348,004 A | 9/1994 | Hollub | 5,558,096 A | 9/1996 | Palatnik |
| 5,348,005 A | 9/1994 | Merrick et al. | 5,560,355 A | 10/1996 | Merchant et al. |
| 5,349,519 A | 9/1994 | Kaestle | 5,564,417 A | 10/1996 | Chance |
| 5,349,952 A | 9/1994 | McCarthy et al. | 5,575,284 A | 11/1996 | Athan et al. |
| 5,349,953 A | 9/1994 | McCarthy et al. | 5,575,285 A | 11/1996 | Takanashi et al. |
| 5,351,685 A | 10/1994 | Potratz | 5,577,500 A | 11/1996 | Potratz |
| 5,353,799 A | 10/1994 | Chance | 5,582,169 A | 12/1996 | Oda et al. |
| 5,355,880 A | 10/1994 | Thomas et al. | 5,584,296 A | 12/1996 | Cui et al. |
| 5,355,882 A | 10/1994 | Ukawa et al. | 5,588,425 A | 12/1996 | Sackner et al. |
| 5,361,758 A | 11/1994 | Hall et al. | 5,588,427 A | 12/1996 | Tien |
| 5,365,066 A | 11/1994 | Krueger, Jr. et al. | 5,590,652 A | 1/1997 | Inai |
| 5,368,025 A | 11/1994 | Young et al. | 5,595,176 A | 1/1997 | Yamaura |
| 5,368,026 A | 11/1994 | Swedlow et al. | 5,596,986 A | 1/1997 | Goldfarb |
| 5,368,224 A | 11/1994 | Richardson et al. | 5,611,337 A | 3/1997 | Bukta |
| 5,372,136 A | 12/1994 | Steuer et al. | 5,617,852 A | 4/1997 | MacGregor |
| 5,377,675 A | 1/1995 | Ruskewicz et al. | 5,619,991 A | 4/1997 | Sloane |
| 5,385,143 A | 1/1995 | Aoyagi | 5,619,992 A | 4/1997 | Guthrie et al. |
| 5,386,827 A | 2/1995 | Chance et al. | 5,626,140 A | 5/1997 | Feldman et al. |
| 5,387,122 A | 2/1995 | Goldberger et al. | 5,630,413 A | 5/1997 | Thomas et al. |
| 5,390,670 A | 2/1995 | Centa et al. | 5,632,272 A | 5/1997 | Diab et al. |
| 5,392,777 A | 2/1995 | Swedlow et al. | 5,632,273 A | 5/1997 | Suzuki |
| 5,398,680 A | 3/1995 | Polson et al. | 5,634,459 A | 6/1997 | Gardosi |
| 5,402,777 A | 4/1995 | Warring et al. | 5,638,593 A | 6/1997 | Gerhardt et al. |
| 5,402,779 A | 4/1995 | Chen et al. | 5,638,816 A | 6/1997 | Kiani-Azarbayjany et al. |
| 5,411,023 A | 5/1995 | Morris, Sr. et al. | 5,638,818 A | 6/1997 | Diab et al. |
| 5,411,024 A | 5/1995 | Thomas et al. | 5,645,060 A | 7/1997 | Yorkey |
| 5,413,099 A | 5/1995 | Schmidt et al. | 5,645,440 A | 7/1997 | Tobler et al. |
| 5,413,100 A | 5/1995 | Barthelemy et al. | 5,660,567 A | 8/1997 | Nierlich et al. |
| 5,413,101 A | 5/1995 | Sugiura | 5,662,105 A | 9/1997 | Tien |
| 5,413,102 A | 5/1995 | Schmidt et al. | 5,662,106 A | 9/1997 | Swedlow et al. |
| 5,417,207 A | 5/1995 | Young et al. | 5,664,270 A | 9/1997 | Bell et al. |
| 5,421,329 A | 6/1995 | Casciani et al. | 5,666,952 A | 9/1997 | Fuse et al. |
| 5,425,360 A | 6/1995 | Nelson | 5,671,529 A | 9/1997 | Nelson |
| 5,425,362 A | 6/1995 | Siker et al. | 5,673,692 A | 10/1997 | Schulze et al. |
| 5,427,093 A | 6/1995 | Ogawa et al. | 5,673,693 A | 10/1997 | Solenberger |
| 5,429,128 A | 7/1995 | Cadell et al. | 5,676,139 A | 10/1997 | Goldberger et al. |
| 5,429,129 A | 7/1995 | Lovejoy et al. | 5,676,141 A | 10/1997 | Hollub |
| 5,431,159 A | 7/1995 | Baker et al. | 5,678,544 A | 10/1997 | DeLonzor et al. |
| 5,431,170 A | 7/1995 | Mathews | 5,680,857 A | 10/1997 | Pelikan et al. |
| 5,437,275 A | 8/1995 | Amundsen et al. | 5,685,299 A | 11/1997 | Diab et al. |
| 5,438,986 A | 8/1995 | Disch et al. | 5,685,301 A | 11/1997 | Klomhaus |
| 5,448,991 A | 9/1995 | Polson et al. | 5,687,719 A | 11/1997 | Sato et al. |
| 5,452,717 A | 9/1995 | Branigan et al. | 5,687,722 A | 11/1997 | Tien et al. |
| 5,465,714 A | 11/1995 | Scheuing | 5,692,503 A | 12/1997 | Kuenstner |
| 5,469,845 A | 11/1995 | DeLonzor et al. | 5,692,505 A | 12/1997 | Fouts |
| RE035,122 E | 12/1995 | Corenman et al. | 5,709,205 A | 1/1998 | Bukta |
| 5,482,034 A | 1/1996 | Lewis et al. | 5,713,355 A | 2/1998 | Richardson et al. |
| 5,482,036 A | 1/1996 | Diab et al. | 5,724,967 A | 3/1998 | Venkatachalam |
| 5,485,847 A | 1/1996 | Baker, Jr. | 5,727,547 A | 3/1998 | Levinson et al. |
| 5,490,505 A | 2/1996 | Diab et al. | 5,730,124 A | 3/1998 | Yamauchi |
| 5,490,523 A | 2/1996 | Isaacson et al. | 5,731,582 A | 3/1998 | West |
| 5,491,299 A | 2/1996 | Naylor et al. | D393,830 S | 4/1998 | Tobler et al. |
| 5,494,032 A | 2/1996 | Robinson et al. | 5,743,260 A | 4/1998 | Chung et al. |
| 5,494,043 A | 2/1996 | O'Sullivan et al. | 5,743,262 A | 4/1998 | Lepper, Jr. et al. |
| 5,497,769 A | 3/1996 | Gratton et al. | 5,743,263 A | 4/1998 | Baker, Jr. |
| 5,497,771 A | 3/1996 | Rosenheimer | 5,746,206 A | 5/1998 | Mannheimer |
| 5,499,627 A | 3/1996 | Steuer et al. | 5,746,697 A | 5/1998 | Swedlow et al. |
| 5,503,148 A | 4/1996 | Pologe et al. | 5,752,914 A | 5/1998 | DeLonzor et al. |
| 5,505,199 A | 4/1996 | Kim | 5,755,226 A | 5/1998 | Carim et al. |
| 5,507,286 A | 4/1996 | Solenberger | 5,758,644 A | 6/1998 | Diab et al. |
| 5,511,546 A | 4/1996 | Hon | 5,760,910 A | 6/1998 | Lepper, Jr. et al. |
| 5,517,988 A | 5/1996 | Gerhard | 5,766,125 A | 6/1998 | Aoyagi et al. |
| 5,520,177 A | 5/1996 | Ogawa et al. | 5,766,127 A | 6/1998 | Pologe et al. |
| 5,521,851 A | 5/1996 | Wei et al. | 5,769,785 A | 6/1998 | Diab et al. |
| 5,522,388 A | 6/1996 | Ishikawa et al. | 5,772,587 A | 6/1998 | Gratton et al. |
| 5,524,617 A | 6/1996 | Mannheimer | 5,774,213 A | 6/1998 | Trebino et al. |
| 5,529,064 A | 6/1996 | Rall et al. | 5,776,058 A | 7/1998 | Levinson et al. |
| 5,533,507 A | 7/1996 | Potratz et al. | 5,776,059 A | 7/1998 | Kaestle |
| 5,551,423 A | 9/1996 | Sugiura | 5,779,630 A | 7/1998 | Fein et al. |
| 5,551,424 A | 9/1996 | Morrison et al. | 5,779,631 A | 7/1998 | Chance |
| 5,553,614 A | 9/1996 | Chance | 5,782,237 A | 7/1998 | Casciani et al. |
| 5,553,615 A | 9/1996 | Carim et al. | 5,782,756 A | 7/1998 | Mannheimer |

| Patent No. | Date | Inventor |
|---|---|---|
| 5,782,757 A | 7/1998 | Diab et al. |
| 5,782,758 A | 7/1998 | Ausec et al. |
| 5,786,592 A | 7/1998 | Hök |
| 5,788,634 A | 8/1998 | Suda et al. |
| 5,790,729 A | 8/1998 | Pologe et al. |
| 5,792,052 A | 8/1998 | Isaacson et al. |
| 5,795,292 A | 8/1998 | Lewis et al. |
| 5,797,841 A | 8/1998 | DeLonzor et al. |
| 5,800,348 A | 9/1998 | Kaestle |
| 5,800,349 A | 9/1998 | Isaacson et al. |
| 5,803,910 A | 9/1998 | Potratz |
| 5,807,246 A | 9/1998 | Sakaguchi et al. |
| 5,807,247 A | 9/1998 | Merchant et al. |
| 5,807,248 A | 9/1998 | Mills |
| 5,810,723 A | 9/1998 | Aldrich |
| 5,810,724 A | 9/1998 | Gronvall |
| 5,813,980 A | 9/1998 | Levinson et al. |
| 5,817,008 A | 10/1998 | Rafert et al. |
| 5,817,009 A | 10/1998 | Rosenheimer et al. |
| 5,817,010 A | 10/1998 | Hibl |
| 5,818,985 A | 10/1998 | Merchant et al. |
| 5,820,550 A | 10/1998 | Polson et al. |
| 5,823,950 A | 10/1998 | Diab et al. |
| 5,823,952 A | 10/1998 | Levinson et al. |
| 5,827,179 A | 10/1998 | Lichter et al. |
| 5,827,182 A | 10/1998 | Raley et al. |
| 5,829,439 A | 11/1998 | Yokosawa et al. |
| 5,830,135 A | 11/1998 | Bosque et al. |
| 5,830,136 A | 11/1998 | DeLonzor et al. |
| 5,830,137 A | 11/1998 | Scharf |
| 5,839,439 A | 11/1998 | Nierlich et al. |
| RE036,000 E | 12/1998 | Swedlow et al. |
| 5,842,979 A | 12/1998 | Jarman |
| 5,842,981 A | 12/1998 | Larsen et al. |
| 5,842,982 A | 12/1998 | Mannheimer |
| 5,846,190 A | 12/1998 | Woehrle |
| 5,851,178 A | 12/1998 | Aronow |
| 5,851,179 A | 12/1998 | Ritson et al. |
| 5,853,364 A | 12/1998 | Baker, Jr. et al. |
| 5,860,919 A | 1/1999 | Kiani-Azarbayjany et al. |
| 5,865,736 A | 2/1999 | Baker, Jr. et al. |
| 5,879,294 A | 3/1999 | Anderson et al. |
| 5,885,213 A | 3/1999 | Richardson et al. |
| 5,890,929 A | 4/1999 | Mills et al. |
| 5,891,021 A | 4/1999 | Dillon et al. |
| 5,891,022 A | 4/1999 | Pologe |
| 5,891,024 A | 4/1999 | Jarman et al. |
| 5,891,025 A | 4/1999 | Buschmann et al. |
| 5,891,026 A | 4/1999 | Wang et al. |
| 5,902,235 A | 5/1999 | Lewis et al. |
| 5,910,108 A | 6/1999 | Solenberger |
| 5,911,690 A | 6/1999 | Rall |
| 5,912,656 A | 6/1999 | Tham et al. |
| 5,913,819 A | 6/1999 | Taylor et al. |
| 5,916,154 A | 6/1999 | Hobbs et al. |
| 5,916,155 A | 6/1999 | Levinson et al. |
| 5,919,133 A | 7/1999 | Taylor et al. |
| 5,919,134 A | 7/1999 | Diab |
| 5,920,263 A | 7/1999 | Huttenhoff et al. |
| 5,921,921 A | 7/1999 | Potratz et al. |
| 5,922,607 A | 7/1999 | Bernreuter |
| 5,924,979 A | 7/1999 | Swedlow et al. |
| 5,924,980 A | 7/1999 | Coetzee |
| 5,924,982 A | 7/1999 | Chin |
| 5,924,985 A | 7/1999 | Jones |
| 5,934,277 A | 8/1999 | Mortz |
| 5,934,925 A | 8/1999 | Tobler et al. |
| 5,940,182 A | 8/1999 | Lepper, Jr. et al. |
| 5,954,644 A | 9/1999 | Dettling et al. |
| 5,957,840 A | 9/1999 | Terasawa et al. |
| 5,960,610 A | 10/1999 | Levinson et al. |
| 5,961,450 A | 10/1999 | Merchant et al. |
| 5,961,452 A | 10/1999 | Chung et al. |
| 5,964,701 A | 10/1999 | Asada et al. |
| 5,971,930 A | 10/1999 | Elghazzawi |
| 5,978,691 A | 11/1999 | Mills |
| 5,978,693 A | 11/1999 | Hamilton et al. |
| 5,983,120 A | 11/1999 | Groner et al. |
| 5,983,122 A | 11/1999 | Jarman et al. |
| 5,987,343 A | 11/1999 | Kinast |
| 5,991,648 A | 11/1999 | Levin |
| 5,995,855 A | 11/1999 | Kiani et al. |
| 5,995,856 A | 11/1999 | Mannheimer et al. |
| 5,995,858 A | 11/1999 | Kinast |
| 5,995,859 A | 11/1999 | Takahashi |
| 5,997,343 A | 12/1999 | Mills et al. |
| 5,999,834 A | 12/1999 | Wang et al. |
| 6,002,952 A | 12/1999 | Diab et al. |
| 6,005,658 A | 12/1999 | Kaluza et al. |
| 6,006,120 A | 12/1999 | Levin |
| 6,011,985 A | 1/2000 | Athan et al. |
| 6,011,986 A | 1/2000 | Diab et al. |
| 6,014,576 A | 1/2000 | Raley et al. |
| 6,018,673 A | 1/2000 | Chin et al. |
| 6,018,674 A | 1/2000 | Aronow |
| 6,022,321 A | 2/2000 | Amano et al. |
| 6,023,541 A | 2/2000 | Merchant et al. |
| 6,026,312 A | 2/2000 | Shemwell et al. |
| 6,026,314 A | 2/2000 | Amerov et al. |
| 6,031,603 A | 2/2000 | Fine et al. |
| 6,035,223 A | 3/2000 | Baker, Jr. |
| 6,036,642 A | 3/2000 | Diab et al. |
| 6,041,247 A | 3/2000 | Weckstrom et al. |
| 6,044,283 A | 3/2000 | Fein et al. |
| 6,047,201 A | 4/2000 | Jackson, III |
| 6,055,447 A | 4/2000 | Well |
| 6,061,584 A | 5/2000 | Lovejoy et al. |
| 6,064,898 A | 5/2000 | Aldrich |
| 6,064,899 A | 5/2000 | Fein et al. |
| 6,067,462 A | 5/2000 | Diab et al. |
| 6,073,038 A | 6/2000 | Wang et al. |
| 6,078,829 A | 6/2000 | Uchida |
| 6,078,833 A | 6/2000 | Hueber |
| 6,081,735 A | 6/2000 | Diab et al. |
| 6,083,157 A | 7/2000 | Noller |
| 6,083,172 A | 7/2000 | Baker, Jr. et al. |
| 6,088,607 A | 7/2000 | Diab et al. |
| 6,094,592 A | 7/2000 | Yorkey et al. |
| 6,095,974 A | 8/2000 | Shemwell et al. |
| 6,104,938 A | 8/2000 | Huiku et al. |
| 6,104,939 A | 8/2000 | Groner |
| 6,112,107 A | 8/2000 | Hannula |
| 6,113,541 A | 9/2000 | Dias et al. |
| 6,115,621 A | 9/2000 | Chin |
| 6,122,535 A | 9/2000 | Kaestle et al. |
| 6,133,994 A | 10/2000 | Mathews et al. |
| 6,135,952 A | 10/2000 | Coetzee |
| 6,144,444 A | 11/2000 | Haworth et al. |
| 6,144,867 A | 11/2000 | Walker et al. |
| 6,144,868 A | 11/2000 | Parker |
| 6,149,481 A | 11/2000 | Wang et al. |
| 6,151,107 A | 11/2000 | Schöllerman et al. |
| 6,151,516 A | 11/2000 | Kiani-Azarbayjany et al. |
| 6,151,518 A | 11/2000 | Hayashi |
| 6,152,754 A | 11/2000 | Gerhardt et al. |
| 6,154,667 A | 11/2000 | Miura et al. |
| 6,157,850 A | 12/2000 | Diab et al. |
| 6,159,147 A | 12/2000 | Lichter |
| 6,163,175 A | 12/2000 | Larsen et al. |
| 6,163,715 A | 12/2000 | Larsen et al. |
| 6,165,005 A | 12/2000 | Mills et al. |
| 6,171,258 B1 | 1/2001 | Karakasoglu et al. |
| 6,173,196 B1 | 1/2001 | Delonzor et al. |
| 6,178,343 B1 | 1/2001 | Bindszus et al. |
| 6,179,159 B1 | 1/2001 | Gurley |
| 6,181,958 B1 | 1/2001 | Steuer et al. |

| Patent | Date | Inventor |
|---|---|---|
| 6,181,959 B1 | 1/2001 | Schöllerman et al. |
| 6,184,521 B1 | 2/2001 | Coffin, IV et al. |
| 6,188,470 B1 | 2/2001 | Grace |
| 6,192,260 B1 | 2/2001 | Chance |
| 6,195,574 B1 * | 2/2001 | Kumar et al. ............... 600/323 |
| 6,195,575 B1 | 2/2001 | Levinson |
| 6,198,951 B1 | 3/2001 | Kosuda et al. |
| 6,206,830 B1 | 3/2001 | Diab et al. |
| 6,213,952 B1 | 4/2001 | Finarov et al. |
| 6,217,523 B1 | 4/2001 | Amano et al. |
| 6,222,189 B1 | 4/2001 | Misner et al. |
| 6,223,064 B1 | 4/2001 | Lynn |
| 6,226,539 B1 | 5/2001 | Potratz |
| 6,226,540 B1 | 5/2001 | Bernreuter et al. |
| 6,229,856 B1 | 5/2001 | Diab et al. |
| 6,230,035 B1 | 5/2001 | Aoyagi et al. |
| 6,233,470 B1 | 5/2001 | Tsuchiya |
| 6,236,871 B1 | 5/2001 | Tsuchiya |
| 6,236,872 B1 | 5/2001 | Diab et al. |
| 6,240,305 B1 | 5/2001 | Tsuchiya |
| 6,253,097 B1 | 6/2001 | Aronow et al. |
| 6,253,098 B1 | 6/2001 | Walker et al. |
| 6,256,523 B1 | 7/2001 | Diab et al. |
| 6,256,524 B1 | 7/2001 | Walker et al. |
| 6,261,236 B1 | 7/2001 | Grimblatov |
| 6,263,221 B1 | 7/2001 | Chance et al. |
| 6,263,222 B1 | 7/2001 | Diab et al. |
| 6,263,223 B1 | 7/2001 | Shepherd et al. |
| 6,266,546 B1 | 7/2001 | Steuer et al. |
| 6,266,547 B1 | 7/2001 | Walker et al. |
| 6,272,363 B1 | 8/2001 | Casciani et al. |
| 6,272,367 B1 | 8/2001 | Chance |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,894 B1 | 9/2001 | Oppelt et al. |
| 6,285,895 B1 | 9/2001 | Ristolainen et al. |
| 6,285,896 B1 | 9/2001 | Tobler et al. |
| 6,298,252 B1 | 10/2001 | Kovach et al. |
| 6,308,089 B1 | 10/2001 | Von der Ruhr et al. |
| 6,321,100 B1 | 11/2001 | Parker |
| 6,330,468 B1 | 12/2001 | Scharf |
| 6,334,065 B1 | 12/2001 | Al-Ali et al. |
| 6,339,715 B1 | 1/2002 | Bahr et al. |
| 6,342,039 B1 | 1/2002 | Lynn |
| 6,343,223 B1 | 1/2002 | Chin et al. |
| 6,343,224 B1 | 1/2002 | Parker |
| 6,349,228 B1 | 2/2002 | Kiani et al. |
| 6,351,658 B1 | 2/2002 | Middleman et al. |
| 6,353,750 B1 | 3/2002 | Kimura |
| 6,356,774 B1 | 3/2002 | Bernstein et al. |
| 6,360,113 B1 | 3/2002 | Dettling |
| 6,360,114 B1 | 3/2002 | Diab et al. |
| 6,361,501 B1 | 3/2002 | Amano et al. |
| 6,363,269 B1 | 3/2002 | Hanna et al. |
| D455,834 S | 4/2002 | Donars et al. |
| 6,370,408 B1 | 4/2002 | Merchant et al. |
| 6,370,409 B1 | 4/2002 | Chung et al. |
| 6,371,921 B1 | 4/2002 | Caro |
| 6,374,129 B1 | 4/2002 | Chin et al. |
| 6,377,829 B1 | 4/2002 | Al-Ali et al. |
| 6,381,479 B1 | 4/2002 | Norris |
| 6,381,480 B1 | 4/2002 | Stoddar et al. |
| 6,385,471 B1 | 5/2002 | Mortz |
| 6,385,821 B1 | 5/2002 | Modgil et al. |
| 6,388,240 B2 | 5/2002 | Schulz et al. |
| 6,393,310 B1 | 5/2002 | Kuenstner |
| 6,393,311 B1 | 5/2002 | Edgar, Jr. et al. |
| 6,397,091 B2 | 5/2002 | Diab et al. |
| 6,397,092 B1 | 5/2002 | Norris et al. |
| 6,397,093 B1 | 5/2002 | Aldrich |
| 6,400,971 B1 | 6/2002 | Finarov et al. |
| 6,400,972 B1 | 6/2002 | Fine |
| 6,400,973 B1 | 6/2002 | Winter |
| 6,402,690 B1 | 6/2002 | Rhee et al. |
| 6,408,198 B1 | 6/2002 | Hanna et al. |
| 6,411,832 B1 | 6/2002 | Guthermann |
| 6,411,833 B1 | 6/2002 | Baker, Jr. et al. |
| 6,421,549 B1 | 7/2002 | Jacques |
| 6,430,423 B2 | 8/2002 | DeLonzor et al. |
| 6,430,513 B1 | 8/2002 | Wang et al. |
| 6,430,525 B1 | 8/2002 | Weber et al. |
| 6,434,408 B1 | 8/2002 | Heckel et al. |
| 6,438,396 B1 | 8/2002 | Cook |
| 6,438,399 B1 | 8/2002 | Kurth |
| 6,449,501 B1 | 9/2002 | Reuss |
| 6,453,183 B1 | 9/2002 | Walker |
| 6,453,184 B1 | 9/2002 | Hyogo et al. |
| 6,456,862 B2 | 9/2002 | Benni |
| 6,461,305 B1 | 10/2002 | Schnall |
| 6,463,310 B1 | 10/2002 | Swedlow et al. |
| 6,463,311 B1 | 10/2002 | Diab |
| 6,466,808 B1 | 10/2002 | Chin et al. |
| 6,466,809 B1 | 10/2002 | Riley |
| 6,470,199 B1 | 10/2002 | Kopotic et al. |
| 6,470,200 B2 | 10/2002 | Walker et al. |
| 6,480,729 B2 | 11/2002 | Stone |
| 6,490,466 B1 | 12/2002 | Fein et al. |
| 6,493,568 B1 | 12/2002 | Bell |
| 6,496,711 B1 | 12/2002 | Athan et al. |
| 6,498,942 B1 | 12/2002 | Esenaliev et al. |
| 6,501,974 B2 | 12/2002 | Huiku |
| 6,501,975 B2 | 12/2002 | Diab et al. |
| 6,505,060 B1 | 1/2003 | Norris |
| 6,505,061 B2 | 1/2003 | Larson |
| 6,505,133 B1 | 1/2003 | Hanna et al. |
| 6,510,329 B2 | 1/2003 | Heckel |
| 6,510,331 B1 | 1/2003 | Williams et al. |
| 6,512,937 B2 | 1/2003 | Blank et al. |
| 6,515,273 B2 | 2/2003 | Al-Ali |
| 6,519,484 B1 | 2/2003 | Lovejoy et al. |
| 6,519,486 B1 | 2/2003 | Edgar, Jr. et al. |
| 6,519,487 B1 | 2/2003 | Parker |
| 6,525,386 B1 | 2/2003 | Mills et al. |
| 6,526,300 B1 | 2/2003 | Kiani et al. |
| 6,526,301 B2 | 2/2003 | Larsen et al. |
| 6,541,756 B2 | 4/2003 | Schulz et al. |
| 6,542,764 B1 | 4/2003 | Al-Ali et al. |
| 6,542,772 B1 | 4/2003 | Chance |
| 6,546,267 B1 | 4/2003 | Sugiura et al. |
| 6,553,241 B2 | 4/2003 | Mannheimer et al. |
| 6,553,242 B1 | 4/2003 | Sarussi |
| 6,553,243 B2 | 4/2003 | Gurley |
| 6,554,788 B1 | 4/2003 | Hunley |
| 6,556,852 B1 | 4/2003 | Schulze et al. |
| 6,560,470 B1 | 5/2003 | Pologe |
| 6,564,077 B2 | 5/2003 | Mortara |
| 6,564,088 B1 | 5/2003 | Soller et al. |
| 6,571,113 B1 | 5/2003 | Fein et al. |
| 6,571,114 B1 | 5/2003 | Koike et al. |
| 6,574,491 B2 | 6/2003 | Elghazzawi |
| 6,580,086 B1 | 6/2003 | Schulz et al. |
| 6,584,336 B1 | 6/2003 | Ali et al. |
| 6,587,703 B2 | 7/2003 | Cheng et al. |
| 6,587,704 B1 | 7/2003 | Fine et al. |
| 6,589,172 B2 | 7/2003 | Williams et al. |
| 6,591,122 B2 | 7/2003 | Schmitt |
| 6,591,123 B2 | 7/2003 | Fein et al. |
| 6,594,511 B2 | 7/2003 | Stone et al. |
| 6,594,512 B2 | 7/2003 | Huang |
| 6,594,513 B1 | 7/2003 | Jobsis et al. |
| 6,596,016 B1 | 7/2003 | Vreman et al. |
| 6,597,931 B1 | 7/2003 | Cheng et al. |
| 6,597,933 B2 | 7/2003 | Kiani et al. |
| 6,600,940 B1 | 7/2003 | Fein et al. |
| 6,606,510 B2 | 8/2003 | Swedlow et al. |

| | | |
|---|---|---|
| 6,606,511 B1 | 8/2003 | Ali et al. |
| 6,606,512 B2 | 8/2003 | Muz et al. |
| 6,608,562 B1 | 8/2003 | Kimura et al. |
| 6,609,016 B1 | 8/2003 | Lynn |
| 6,615,064 B1 | 9/2003 | Aldrich |
| 6,615,065 B1 | 9/2003 | Barrett et al. |
| 6,618,602 B2 | 9/2003 | Levin et al. |
| 6,618,614 B1 | 9/2003 | Chance |
| 6,622,034 B1 | 9/2003 | Gorski et al. |
| 6,628,975 B1 | 9/2003 | Fein et al. |
| 6,631,281 B1 | 10/2003 | Kästle |
| 6,632,181 B2 | 10/2003 | Flaherty |
| 6,640,116 B2 | 10/2003 | Diab |
| 6,643,530 B2 | 11/2003 | Diab et al. |
| 6,643,531 B1 | 11/2003 | Katarow |
| 6,647,279 B2 | 11/2003 | Pologe |
| 6,647,280 B2 | 11/2003 | Bahr et al. |
| 6,650,916 B2 | 11/2003 | Cook |
| 6,650,917 B2 | 11/2003 | Diab et al. |
| 6,650,918 B2 | 11/2003 | Terry |
| 6,654,621 B2 | 11/2003 | Palatnik et al. |
| 6,654,622 B1 | 11/2003 | Eberhard et al. |
| 6,654,623 B1 | 11/2003 | Kästle |
| 6,654,624 B2 | 11/2003 | Diab et al. |
| 6,658,276 B2 | 12/2003 | Kianl et al. |
| 6,658,277 B2 | 12/2003 | Wasserman |
| 6,662,033 B2 | 12/2003 | Casciani et al. |
| 6,665,551 B1 | 12/2003 | Suzuki |
| 6,668,182 B2 | 12/2003 | Hubelbank |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,671,530 B2 | 12/2003 | Chung et al. |
| 6,671,531 B2 | 12/2003 | Al-Ali et al. |
| 6,671,532 B1 | 12/2003 | Fudge et al. |
| 6,675,031 B1 | 1/2004 | Porges et al. |
| 6,678,543 B2 | 1/2004 | Diab et al. |
| 6,681,126 B2 | 1/2004 | Solenberger |
| 6,681,128 B2 | 1/2004 | Steuer et al. |
| 6,681,454 B2 | 1/2004 | Modgil et al. |
| 6,684,090 B2 | 1/2004 | Ali et al. |
| 6,684,091 B2 | 1/2004 | Parker |
| 6,694,160 B2 | 2/2004 | Chin |
| 6,697,653 B2 | 2/2004 | Hanna |
| 6,697,655 B2 | 2/2004 | Sueppel et al. |
| 6,697,656 B1 | 2/2004 | Al-Ali |
| 6,697,658 B2 | 2/2004 | Al-Ali |
| RE038,476 E | 3/2004 | Diab et al. |
| 6,699,194 B1 | 3/2004 | Diab et al. |
| 6,699,199 B2 | 3/2004 | Asada et al. |
| 6,701,170 B2 | 3/2004 | Stetson |
| 6,702,752 B2 | 3/2004 | Dekker |
| 6,707,257 B2 | 3/2004 | Norris |
| 6,708,049 B1 | 3/2004 | Berson et al. |
| 6,709,402 B2 | 3/2004 | Dekker |
| 6,711,424 B1 | 3/2004 | Fine et al. |
| 6,711,425 B1 | 3/2004 | Reuss |
| 6,711,426 B2 | 3/2004 | Benaron et al. |
| 6,712,762 B1 | 3/2004 | Lichter |
| 6,714,803 B1 | 3/2004 | Mortz |
| 6,714,804 B2 | 3/2004 | Al-Ali et al. |
| 6,714,805 B2 | 3/2004 | Jeon et al. |
| RE038,492 E | 4/2004 | Diab et al. |
| 6,719,686 B2 | 4/2004 | Coakley et al. |
| 6,719,705 B2 | 4/2004 | Mills |
| 6,720,734 B2 | 4/2004 | Norris |
| 6,721,584 B2 | 4/2004 | Baker, Jr. et al. |
| 6,721,585 B1 | 4/2004 | Parker |
| 6,725,074 B1 | 4/2004 | Kästle |
| 6,725,075 B2 | 4/2004 | Al-Ali |
| 6,731,962 B1 | 5/2004 | Katarow |
| 6,731,963 B2 | 5/2004 | Finarov et al. |
| 6,731,967 B1 | 5/2004 | Turcott |
| 6,735,459 B2 | 5/2004 | Parker |
| 6,745,060 B2 | 6/2004 | Diab et al. |
| 6,745,061 B1 | 6/2004 | Hicks et al. |
| 6,748,253 B2 | 6/2004 | Norris et al. |
| 6,748,254 B2 | 6/2004 | O'Neill et al. |
| 6,754,515 B1 | 6/2004 | Pologe |
| 6,754,516 B2 | 6/2004 | Mannheimer |
| 6,760,607 B2 | 7/2004 | Al-Ali |
| 6,760,609 B2 | 7/2004 | Jacques |
| 6,760,610 B2 | 7/2004 | Tscupp et al. |
| 6,763,255 B2 | 7/2004 | DeLonzor et al. |
| 6,763,256 B2 | 7/2004 | Kimball et al. |
| 6,770,028 B1 | 8/2004 | Ali et al. |
| 6,771,994 B2 | 8/2004 | Kiani et al. |
| 6,773,397 B2 | 8/2004 | Kelly |
| 6,778,923 B2 | 8/2004 | Norris et al. |
| 6,780,158 B2 | 8/2004 | Yarita |
| 6,791,689 B1 | 9/2004 | Weckstrom |
| 6,792,300 B1 | 9/2004 | Diab et al. |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,801,802 B2 | 10/2004 | Sitzman et al. |
| 6,802,812 B1 | 10/2004 | Walker et al. |
| 6,805,673 B2 | 10/2004 | Dekker |
| 6,810,277 B2 | 10/2004 | Edgar, Jr. et al. |
| 6,813,511 B2 | 11/2004 | Diab et al. |
| 6,816,266 B2 | 11/2004 | Varshneya et al. |
| 6,816,741 B2 | 11/2004 | Diab |
| 6,819,950 B2 | 11/2004 | Mills |
| 6,822,564 B2 | 11/2004 | Al-Ali |
| 6,825,619 B2 | 11/2004 | Norris |
| 6,826,419 B2 | 11/2004 | Diab et al. |
| 6,829,496 B2 | 12/2004 | Nagai et al. |
| 6,830,711 B2 | 12/2004 | Mills et al. |
| 6,836,679 B2 | 12/2004 | Baker, Jr. et al. |
| 6,839,579 B1 | 1/2005 | Chin |
| 6,839,580 B2 | 1/2005 | Zonios et al. |
| 6,839,582 B2 | 1/2005 | Heckel |
| 6,839,659 B2 | 1/2005 | Tarassenko et al. |
| 6,842,635 B1 | 1/2005 | Parker |
| 6,845,256 B2 | 1/2005 | Chin et al. |
| 6,850,787 B2 | 2/2005 | Weber et al. |
| 6,850,788 B2 | 2/2005 | Al-Ali |
| 6,850,789 B2 | 2/2005 | Schweitzer, Jr. et al. |
| 6,861,639 B2 | 3/2005 | Al-Ali |
| 6,862,091 B2 | 3/2005 | Johnson |
| 6,863,652 B2 | 3/2005 | Huang et al. |
| 6,865,407 B2 | 3/2005 | Kimball et al. |
| 6,879,850 B2 | 4/2005 | Kimball |
| 6,882,874 B2 | 4/2005 | Huiku |
| 6,898,452 B2 | 5/2005 | Al-Ali et al. |
| 6,909,912 B2 | 6/2005 | Melker et al. |
| 6,912,413 B2 | 6/2005 | Rantala et al. |
| 6,920,345 B2 | 7/2005 | Al-Ali et al. |
| 6,931,269 B2 | 8/2005 | Terry |
| 6,934,570 B2 | 8/2005 | Kiani et al. |
| 6,934,571 B2 | 8/2005 | Wiesmann et al. |
| 6,941,162 B2 | 9/2005 | Fudge et al. |
| 6,947,781 B2 | 9/2005 | Asada et al. |
| 6,950,687 B2 | 9/2005 | Al-Ali |
| 6,954,664 B2 | 10/2005 | Sweitzer |
| 6,968,221 B2 | 11/2005 | Rosenthal |
| 6,979,812 B2 | 12/2005 | Al-Ali |
| 6,983,178 B2 | 1/2006 | Fine et al. |
| 6,985,763 B2 | 1/2006 | Boas et al. |
| 6,985,764 B2 | 1/2006 | Mason et al. |
| 6,990,365 B1 | 1/2006 | Parker et al. |
| 6,990,426 B2 | 1/2006 | Yoon et al. |
| 6,992,751 B2 | 1/2006 | Okita et al. |
| 6,992,772 B2 | 1/2006 | Block |
| 6,993,371 B2 | 1/2006 | Kiani et al. |
| 6,993,372 B2 | 1/2006 | Fine et al. |

| Patent/Publication | Date | Inventor |
|---|---|---|
| 6,996,427 B2 | 2/2006 | Ali et al. |
| 7,003,338 B2 | 2/2006 | Weber et al. |
| 7,003,339 B2 | 2/2006 | Diab et al. |
| 7,006,855 B1 | 2/2006 | Sarussi |
| 7,006,856 B2 | 2/2006 | Baker, Jr. et al. |
| 7,010,341 B2 | 3/2006 | Chance |
| 7,016,715 B2 | 3/2006 | Stetson |
| 7,020,507 B2 | 3/2006 | Scharf et al. |
| 7,024,233 B2 | 4/2006 | Ali et al. |
| 7,024,235 B2 | 4/2006 | Melker et al. |
| 7,025,728 B2 | 4/2006 | Ito et al. |
| 7,027,849 B2 | 4/2006 | Al-Ali |
| 7,027,850 B2 | 4/2006 | Wasserman |
| 7,039,449 B2 | 5/2006 | Al-Ali |
| 7,043,289 B2 | 5/2006 | Fine et al. |
| 7,047,054 B2 | 5/2006 | Benni |
| 7,047,055 B2 | 5/2006 | Boas et al. |
| 7,060,035 B2 | 6/2006 | Wasserman |
| 7,062,307 B2 | 6/2006 | Norris et al. |
| 7,067,893 B2 | 6/2006 | Mills et al. |
| 7,072,701 B2 | 7/2006 | Chen et al. |
| 7,072,702 B2 | 7/2006 | Edgar, Jr. et al. |
| 7,079,880 B2 | 7/2006 | Stetson |
| 7,085,597 B2 | 8/2006 | Fein et al. |
| 7,096,052 B2 | 8/2006 | Mason et al. |
| 7,096,054 B2 | 8/2006 | Abdul-Hafiz et al. |
| 7,107,088 B2 | 9/2006 | Aceti |
| 7,107,116 B2 | 9/2006 | Geng |
| 7,113,815 B2 | 9/2006 | O'Neil et al. |
| 7,117,590 B2 | 10/2006 | Koenig et al. |
| 7,123,950 B2 | 10/2006 | Mannheimer |
| 7,127,278 B2 | 10/2006 | Melker et al. |
| 7,130,671 B2 | 10/2006 | Baker, Jr. et al. |
| 7,132,641 B2 | 11/2006 | Schulz et al. |
| 7,133,711 B2 | 11/2006 | Chernoguz et al. |
| 7,134,754 B2 | 11/2006 | Kerr et al. |
| 7,139,559 B2 | 11/2006 | Kenagy et al. |
| 7,139,603 B2 | 11/2006 | Chance |
| 7,142,901 B2 | 11/2006 | Kiani et al. |
| 7,162,288 B2 | 1/2007 | Nordstrom et al. |
| 7,171,065 B2 | 1/2007 | Lee et al. |
| 7,190,987 B2 | 3/2007 | Kindekugel et al. |
| 7,198,778 B2 | 4/2007 | Achilefu et al. |
| 7,215,984 B2 | 5/2007 | Diab et al. |
| 7,225,006 B2 | 5/2007 | Al-Ali et al. |
| 7,228,161 B2 | 6/2007 | Chin |
| 7,236,881 B2 | 6/2007 | Schmitt et al. |
| 7,248,910 B2 | 7/2007 | Li et al. |
| 7,251,518 B2 | 7/2007 | Herrmann |
| 7,254,427 B2 | 8/2007 | Cho et al. |
| 7,254,433 B2 | 8/2007 | Diab et al. |
| 7,254,434 B2 | 8/2007 | Schulz et al. |
| 7,272,425 B2 | 9/2007 | Al-Ali |
| 7,280,858 B2 | 10/2007 | Al-Ali et al. |
| 7,283,242 B2 | 10/2007 | Thornton |
| 7,295,866 B2 | 11/2007 | Al-Ali |
| 7,305,262 B2 | 12/2007 | Brodnick et al. |
| 7,315,753 B2 | 1/2008 | Baker, Jr. et al. |
| 7,330,746 B2 | 2/2008 | Demuth et al. |
| 7,341,559 B2 | 3/2008 | Schulz et al. |
| 7,341,560 B2 | 3/2008 | Henderson et al. |
| 7,343,186 B2 | 3/2008 | Lamego et al. |
| 7,400,918 B2 | 7/2008 | Parker et al. |
| 7,424,317 B2 | 9/2008 | Parker et al. |
| 7,457,652 B2 | 11/2008 | Porges et al. |
| 2002/0016537 A1 | 2/2002 | Muz et al. |
| 2002/0026109 A1 | 2/2002 | Diab et al. |
| 2002/0028990 A1 | 3/2002 | Shepherd et al. |
| 2002/0038078 A1 | 3/2002 | Ito |
| 2002/0042558 A1 | 4/2002 | Mendelson |
| 2002/0068859 A1 | 6/2002 | Knopp |
| 2002/0072681 A1 | 6/2002 | Schnall |
| 2002/0116797 A1 | 8/2002 | Modgil et al. |
| 2002/0128544 A1 | 9/2002 | Diab et al. |
| 2002/0133067 A1 | 9/2002 | Jackson, III |
| 2002/0156354 A1 | 10/2002 | Larson |
| 2002/0173706 A1 | 11/2002 | Takatani |
| 2002/0190863 A1 | 12/2002 | Lynn |
| 2003/0018243 A1 | 1/2003 | Gerhardt et al. |
| 2003/0036690 A1 | 2/2003 | Geddes et al. |
| 2003/0045785 A1 | 3/2003 | Diab et al. |
| 2003/0073889 A1 | 4/2003 | Keilbach et al. |
| 2003/0073890 A1 | 4/2003 | Hanna |
| 2003/0100840 A1 | 5/2003 | Sugiura et al. |
| 2003/0187337 A1 | 10/2003 | Tarassenko et al. |
| 2003/0197679 A1 | 10/2003 | Ali et al. |
| 2003/0208112 A1* | 11/2003 | Schmidt et al. ............. 600/313 |
| 2003/0212316 A1 | 11/2003 | Leiden et al. |
| 2003/0225323 A1 | 12/2003 | Kiani et al. |
| 2004/0006261 A1 | 1/2004 | Swedlow et al. |
| 2004/0024326 A1 | 2/2004 | Yeo et al. |
| 2004/0039272 A1 | 2/2004 | Abdul-Hafiz et al. |
| 2004/0039273 A1 | 2/2004 | Terry |
| 2004/0054291 A1 | 3/2004 | Schulz et al. |
| 2004/0068164 A1 | 4/2004 | Diab et al. |
| 2004/0092805 A1 | 5/2004 | Yarita |
| 2004/0097797 A1 | 5/2004 | Porges et al. |
| 2004/0098009 A1 | 5/2004 | Boecker et al. |
| 2004/0117891 A1 | 6/2004 | Hannula et al. |
| 2004/0147824 A1 | 7/2004 | Diab et al. |
| 2004/0158134 A1 | 8/2004 | Diab et al. |
| 2004/0162472 A1 | 8/2004 | Berson et al. |
| 2004/0167381 A1 | 8/2004 | Lichter |
| 2004/0186358 A1 | 9/2004 | Chernow et al. |
| 2004/0204637 A1 | 10/2004 | Diab et al. |
| 2004/0204638 A1 | 10/2004 | Diab et al. |
| 2004/0204639 A1 | 10/2004 | Casciani et al. |
| 2004/0204865 A1 | 10/2004 | Lee et al. |
| 2004/0210146 A1 | 10/2004 | Diab et al. |
| 2004/0215085 A1 | 10/2004 | Schnall |
| 2004/0230108 A1 | 11/2004 | Melker et al. |
| 2004/0236196 A1 | 11/2004 | Diab et al. |
| 2005/0004479 A1 | 1/2005 | Townsend et al. |
| 2005/0014999 A1 | 1/2005 | Rahe-Meyer |
| 2005/0020887 A1 | 1/2005 | Goldberg |
| 2005/0033131 A1 | 2/2005 | Chen |
| 2005/0043599 A1 | 2/2005 | O'Mara |
| 2005/0043600 A1 | 2/2005 | Diab et al. |
| 2005/0049468 A1 | 3/2005 | Carlson |
| 2005/0065415 A1 | 3/2005 | Cho et al. |
| 2005/0070773 A1 | 3/2005 | Chin |
| 2005/0075546 A1 | 4/2005 | Samsoondar |
| 2005/0075550 A1 | 4/2005 | Lindekugel |
| 2005/0084202 A1 | 4/2005 | Smith et al. |
| 2005/0085704 A1 | 4/2005 | Schulz |
| 2005/0090720 A1 | 4/2005 | Wu |
| 2005/0113704 A1 | 5/2005 | Lawson et al. |
| 2005/0119543 A1 | 6/2005 | Parker |
| 2005/0131286 A1 | 6/2005 | Parker et al. |
| 2005/0163412 A1 | 7/2005 | Glebov et al. |
| 2005/0197548 A1 | 9/2005 | Dietiker |
| 2005/0228248 A1 | 10/2005 | Dietiker |
| 2005/0256386 A1 | 11/2005 | Chan |
| 2005/0267346 A1 | 12/2005 | Faber et al. |
| 2005/0272986 A1 | 12/2005 | Smith |
| 2005/0277819 A1 | 12/2005 | Kiani et al. |
| 2006/0020179 A1 | 1/2006 | Anderson |
| 2006/0030764 A1 | 2/2006 | Porges |
| 2006/0058594 A1 | 3/2006 | Ishizuka et al. |
| 2006/0058690 A1 | 3/2006 | Bartnik et al. |
| 2006/0074280 A1 | 4/2006 | Martis |
| 2006/0084852 A1 | 4/2006 | Mason et al. |
| 2006/0084878 A1 | 4/2006 | Banet |
| 2006/0089547 A1 | 4/2006 | Sarussi |
| 2006/0106294 A1 | 5/2006 | Maser et al. |
| 2006/0122517 A1 | 6/2006 | Banet |

| | | | | | | |
|---|---|---|---|---|---|---|
| 2006/0129039 A1 | 6/2006 | Lindner | | GB | 2 259 545 | 3/1993 |
| 2006/0155198 A1 | 7/2006 | Schmid | | JP | 63275325 | 11/1988 |
| 2006/0173257 A1 | 8/2006 | Nagai | | JP | 2013450 | 1/1990 |
| 2006/0176471 A1 | 8/2006 | Hendriks et al. | | JP | 2111343 | 4/1990 |
| 2006/0224058 A1 | 10/2006 | Mannheimer | | JP | 02 191434 | 7/1990 |
| 2006/0276697 A1 | 12/2006 | Demuth et al. | | JP | 2237544 | 9/1990 |
| 2007/0032710 A1 | 2/2007 | Raridan et al. | | JP | 03 173536 | 7/1991 |
| 2007/0032712 A1 | 2/2007 | Raridan et al. | | JP | 3170866 | 7/1991 |
| 2007/0032715 A1 | 2/2007 | Eghbal et al. | | JP | 3245042 | 10/1991 |
| 2007/0049813 A1 | 3/2007 | Blouin | | JP | 4174648 | 6/1992 |
| 2007/0060808 A1 | 3/2007 | Hoarau | | JP | 4191642 | 7/1992 |
| 2007/0073121 A1 | 3/2007 | Hoarau et al. | | JP | 4332536 | 11/1992 |
| 2007/0073122 A1 | 3/2007 | Hoarau | | JP | 3124073 | 3/1993 |
| 2007/0073125 A1 | 3/2007 | Hoarau et al. | | JP | 5049624 | 3/1993 |
| 2007/0073126 A1 | 3/2007 | Raridan | | JP | 5049625 | 3/1993 |
| 2007/0073128 A1 | 3/2007 | Hoarau | | JP | 3115374 | 4/1993 |
| 2007/0078315 A1 | 4/2007 | Kling et al. | | JP | 05 200031 | 8/1993 |
| 2007/0078316 A1 | 4/2007 | Hoarau | | JP | 2005/200031 | 8/1993 |
| 2007/0260129 A1 | 11/2007 | Chin | | JP | 5212016 | 8/1993 |
| 2007/0260130 A1 | 11/2007 | Chin | | JP | 06 014906 | 1/1994 |
| 2007/0260131 A1 | 11/2007 | Chin | | JP | 06014906 | 1/1994 |
| 2007/0299328 A1 | 12/2007 | Chin et al. | | JP | 6016774 | 3/1994 |

FOREIGN PATENT DOCUMENTS

| | | | | | |
|---|---|---|---|---|---|
| JP | 3116255 | 4/1994 |
| JP | 6029504 | 4/1994 |
| JP | 6098881 | 4/1994 |
| DE | 3516338 | 11/1986 | JP | 06 154177 | 6/1994 |
| DE | 37 03 458 | 8/1988 | JP | 6269430 | 9/1994 |
| DE | 3938759 | 5/1991 | JP | 6285048 | 10/1994 |
| DE | 4210102 | 9/1993 | JP | 7001273 | 1/1995 |
| DE | 4423597 | 8/1995 | JP | 7124138 | 5/1995 |
| DE | 19632361 | 2/1997 | JP | 7136150 | 5/1995 |
| DE | 69123448 | 5/1997 | JP | 3116259 | 6/1995 |
| DE | 19703220 | 7/1997 | JP | 3116260 | 6/1995 |
| DE | 19640807 | 9/1997 | JP | 7155311 | 6/1995 |
| DE | 19647877 | 4/1998 | JP | 7155313 | 6/1995 |
| DE | 10030862 | 1/2002 | JP | 3238813 | 7/1995 |
| DE | 20318882 | 4/2004 | JP | 7171139 | 7/1995 |
| EP | 0127947 | 5/1984 | JP | 3134144 | 9/1995 |
| EP | 00194105 | 9/1986 | JP | 7236625 | 9/1995 |
| EP | 00204459 | 12/1986 | JP | 7246191 | 9/1995 |
| EP | 0 262 779 | 4/1988 | JP | 8256996 | 10/1996 |
| EP | 0315040 | 10/1988 | JP | 9192120 | 7/1997 |
| EP | 0314331 | 5/1989 | JP | 10216113 | 8/1998 |
| EP | 00352923 | 1/1990 | JP | 10216114 | 8/1998 |
| EP | 0 360 977 | 4/1990 | JP | 10216115 | 8/1998 |
| EP | 00430340 | 6/1991 | JP | 10337282 | 12/1998 |
| EP | 0435 500 | 7/1991 | JP | 11019074 | 1/1999 |
| EP | 0572684 | 5/1992 | JP | 11155841 | 6/1999 |
| EP | 00497021 | 8/1992 | JP | 11 188019 | 7/1999 |
| EP | 0529412 | 8/1992 | JP | 11244268 | 9/1999 |
| EP | 0531631 | 9/1992 | JP | 20107157 | 4/2000 |
| EP | 0566354 | 4/1993 | JP | 20237170 | 9/2000 |
| EP | 0587009 | 8/1993 | JP | 21245871 | 9/2001 |
| EP | 00630203 | 9/1993 | JP | 22224088 | 8/2002 |
| EP | 0 572 684 | 12/1993 | JP | 22282242 | 10/2002 |
| EP | 00615723 | 9/1994 | JP | 23153881 | 5/2003 |
| EP | 702931 | 3/1996 | JP | 23153882 | 5/2003 |
| EP | 00702931 | 3/1996 | JP | 23169791 | 6/2003 |
| EP | 00724860 | 8/1996 | JP | 23194714 | 7/2003 |
| EP | 00793942 | 9/1997 | JP | 23210438 | 7/2003 |
| EP | 0 864 293 | 9/1998 | JP | 23275192 | 9/2003 |
| EP | 01006863 | 10/1998 | JP | 23339678 | 12/2003 |
| EP | 01006864 | 10/1998 | JP | 24008572 | 1/2004 |
| EP | 0875199 | 11/1998 | JP | 24089546 | 3/2004 |
| EP | 00998214 | 12/1998 | JP | 24113353 | 4/2004 |
| EP | 0 898 933 | 3/1999 | JP | 24135854 | 5/2004 |
| EP | 0898933 | 3/1999 | JP | 24148069 | 5/2004 |
| EP | 630203 | 7/2002 | JP | 24148070 | 5/2004 |
| EP | 01332713 | 8/2003 | JP | 24159810 | 6/2004 |
| EP | 01469773 | 8/2003 | JP | 24166775 | 6/2004 |
| EP | 1502529 | 7/2004 | JP | 24194908 | 7/2004 |
| EP | 01491135 | 12/2004 | JP | 24202190 | 7/2004 |
| FR | 2685865 | 1/1992 | JP | 24248819 | 9/2004 |

| | | |
|---|---|---|
| JP | 24248820 | 9/2004 |
| JP | 24261364 | 9/2004 |
| JP | 24290412 | 10/2004 |
| JP | 24290544 | 10/2004 |
| JP | 24290545 | 10/2004 |
| JP | 24329406 | 11/2004 |
| JP | 24329607 | 11/2004 |
| JP | 24329928 | 11/2004 |
| JP | 24337605 | 12/2004 |
| JP | 24344367 | 12/2004 |
| JP | 24351107 | 12/2004 |
| JP | 25034472 | 2/2005 |
| WO | WO 98/09566 | 10/1989 |
| WO | WO 90/01293 | 2/1990 |
| WO | WO9001293 | 2/1990 |
| WO | WO 90/04352 | 5/1990 |
| WO | WO 91/01678 | 2/1991 |
| WO | WO 91/11137 | 8/1991 |
| WO | WO 92/00513 | 1/1992 |
| WO | WO 92/21281 | 12/1992 |
| WO | WO 93/09711 | 5/1993 |
| WO | WO 93/13706 | 7/1993 |
| WO | WO 93/16629 | 9/1993 |
| WO | WO 94/03102 | 2/1994 |
| WO | WO 94/23643 | 10/1994 |
| WO | WO 95/02358 | 1/1995 |
| WO | WO 95/12349 | 5/1995 |
| WO | WO 95/16970 | 6/1995 |
| WO | WO 96/13208 | 5/1996 |
| WO | WO 96/39927 | 12/1996 |
| WO | WO 97/36536 | 10/1997 |
| WO | WO 97/36538 | 10/1997 |
| WO | WO 97/49330 | 12/1997 |
| WO | WO 98/17174 | 4/1998 |
| WO | WO 98/18382 | 5/1998 |
| WO | WO 98/43071 | 10/1998 |
| WO | WO 98/51212 | 11/1998 |
| WO | WO 98/57577 | 12/1998 |
| WO | WO 99/00053 | 1/1999 |
| WO | WO 99/32030 | 7/1999 |
| WO | WO 99/47039 | 9/1999 |
| WO | WO 99/63884 | 12/1999 |
| WO | WO 00/21438 | 4/2000 |
| WO | WO 00/28888 | 5/2000 |
| WO | WO 00/59374 | 10/2000 |
| WO | WO 01/13790 | 3/2001 |
| WO | WO 01/16577 | 3/2001 |
| WO | WO 01/17421 | 3/2001 |
| WO | WO 01/47426 | 3/2001 |
| WO | WO 01/40776 | 6/2001 |
| WO | WO 01/67946 | 9/2001 |
| WO | WO 01/76461 | 10/2001 |
| WO | WO 02/14793 | 2/2002 |
| WO | WO 02/35999 | 5/2002 |
| WO | WO 02/062213 | 8/2002 |
| WO | WO 02/074162 | 9/2002 |
| WO | WO 02/085202 | 10/2002 |
| WO | WO 03/000125 | 1/2003 |
| WO | WO 03/01180 | 1/2003 |
| WO | WO 03/009750 | 2/2003 |
| WO | WO 03/011127 | 2/2003 |
| WO | WO 03/020129 | 3/2003 |
| WO | WO 03/039326 | 5/2003 |
| WO | WO 03/063697 | 8/2003 |
| WO | WO 03/073924 | 9/2003 |
| WO | WO 04/000114 | 12/2003 |
| WO | WO 2004/006748 | 1/2004 |
| WO | WO 2004/069046 | 8/2004 |
| WO | WO 2004/075746 | 9/2004 |
| WO | WO 2005/002434 | 1/2005 |
| WO | WO 2005/009221 | 2/2005 |
| WO | WO 2005/010567 | 2/2005 |
| WO | WO 2005/010568 | 2/2005 |
| WO | WO 2005/020120 | 3/2005 |
| WO | WO 2005025399 | 3/2005 |
| WO | WO 2005/065540 | 7/2005 |
| WO | WO 2006097910 | 9/2006 |

OTHER PUBLICATIONS

Rheineck-Leyssius, Aart t., et al.; "Advanced Pulse Oximeter Signal Processing Technology Compared to Simple Averaging: I. Effect on Frequency of Alarms in the Operating Room," *Journal of clinical Anestesia*, vol. 11, pp:192-195 (1990).

Zahar, N., et al.; "Automatic Feedback Control of Oxygen Therapy Using Pulse Oximetry," *Annual International Conference of the IEEE Engineering in Medicine and Biology Society*, vol. 13, No. 4, pp. 1614-1615 (1991).

Aoyagi, T., et al.; "Analysis of Motion Artifacts in Pulse Oximetry," *Japanese Society Me*, vol. 42, p. 20 (1993) (Article in Japanese — contains English summary of article).

Barreto, A.B., et al.; "Adaptive Cancelation of Motion artifact in Photoplethysmographic Blood Volume Pulse Measurements for Exercise Evaluation," *IEEE-EMBC and CMBEC—Theme 4: Signal Processing*, pp. 983-984 (1995).

Vincente, L.M., et al.; "Adaptive Pre-Processing of Photoplethysmographic Blood Volume Pulse Measurements," pp. 114-117 (1996).

Plummer, John L., et al.; "Identification of Movement Artifact by the Nellcor N-200 and N-3000 Pulse Oximeters," *Journal of clinical Monitoring*, vol. 13, pp. 109-113 (1997).

Barnum, P.T., et al.; "Novel Pulse Oximetry Technology Capable of Reliable Bradycardia Monitoring in the Neonate," *Respiratory Care*, vol. 42, No. 1, p. 1072 (Nov. 1997).

Poets, C. F., et al.; "Detection of movement artifact in recorded pulse oximeter saturation," *Eur. J. Pediatr.*; vol. 156, pp. 808-811 (1997).

Masin, Donald I., et al.; "Fetal Transmission Pulse Oximetry," *Proceedings 19th International Conference IEEE/EMBS*, Oct. 30-Nov. 2, 1997; pp. 2326-2329.

Block, Frank E., Jr., et al.; "Technology evaluation report: Obtaining pulse oximeter signals when the usual probe cannot be used," *International journal of clinical Monitoring and Computing*, vol. 14, pp. 23-28 (1997).

Nijland, Roel, et al.; "Validation of Reflectance Pulse Oximetry: An Evaluation of a new Sensor in Piglets," *Journal of Clinical Monitoring*, vol. 13, pp. 43-49 (1997).

Soto, Denise A.; "A Comparative Study of Pulse Oximeter Measurements: Digit Versus Earlobe," Master of Science Thesis, California State University Dominguez Hills, May 1997, 46 pgs.

Faisst, Karin, et al.; "Intrapartum Reflectance Pulse Oximetry: Effects of Sensor Location and Fixation Duration on Oxygen Saturation Readings," *Journal of Clinical Monitoring*, vol. 13, pp. 299-302 (1997).

Izumi, Akio, et al.; "Accuracy and Utility of a New Reflectance Pulse Oximeter for Fetal Monitoring During Labor," *Journal of Clinical Monitoring*, vol. 13, pp. 103-108( 1997).

Mannheimer, Paul D., et al.; "Wavelength Selection for Low-Saturation Pulse Oximetry," *IEEE Transactions on Biomedical Engineering*, vol. 44, No. 3, pp. 148-158 (Mar. 1997).

"Smaller Product, Tighter Tolerances Pose Dispensing Challenges for Medical Device Manufacturer," *Adhesives Age*, pp. 40-41 (Oct. 1997).

Buschman, J.P., et al.; "Principles and Problems of Calibration of Fetal Oximeters," *Biomedizinische Technik*, vol. 42, pp. 265-266 (1997).

Pickett, John, et al.; "Pulse Oximetry and PPG Measurements in Plastic Surgery," *Proceedings—19th International Conference—IEEE/EMBS*, Chicago, Illinois, Oct. 30-Nov. 2, 1997, pp. 2330-2332.

Leahy, Martin J., et al.; "Sensor Validation in Biomedical Applications," *IFAC Modelling and Control in Biomedical Systems*, Warwick, UK; pp. 221-226 (1997).

Barreto, Armando B., et al.; "Adaptive LMS Delay Measurement in dual Blood Volume Pulse Signals for Non-Invasive Monitoring," *IEEE*, pp. 117-120 (1997).

Crilly, Paul B., et al.; "An Integrated Pulse Oximeter System for Telemedicine Applications," *IEEE Instrumentation and Measurement Technology Conference*, Ottawa, Canada; May 19-21, 1997; pp. 102-104.

DeKock, Marc; "Pulse Oximetry Probe Adhesive Disks: a Potential for Infant Aspiration," *Anesthesiology*, vol. 89, pp. 1603-1604 (1998).

East, Christine E., et al.; "Fetal Oxygen Saturation and Uterine Contractions During Labor," *American Journal of Perinatology*, vol. 15, No. 6, pp. 345-349 (Jun. 1998).

Rhee, Sokwoo, et al.; "The Ring Sensor: a New Ambulatory Wearable Sensor for Twenty-Four Hour Patient Monitoring," *Proceedings of the 20th annual International Conference of the IEEE Engineering in Medicine and Biology Society*, vol. 20, No. 4, pp. 1906-1909 (Oct. 1998).

Yang, Boo-Ho, et al.; "A Twenty-Four Hour Tele-Nursing System Using a Ring Sensor," *Proceedings of the 1998 IEEE International Conference on Robotics & Automation*, Leaven, Belgium, May 1998; pp. 387-392.

König, Volker, et al.; "Reflectance Pulse Oximetry—Principles and Obstetric Application in the Zurich System," *Journal of Clinical Monitoring and Computing*, vol. 14, pp. 403-412 (1998).

Nogawa, Masamichi, et al.; "A Novel Hybrid Reflectance Pulse Oximater Sensor with improved Linearity and General Applicability to Various Portions of the Body," *Proceedings of the 20th Annual International Conference of the IEEE Engineering in Medicine and Biology Society*, vol. 20, No. 4, pp. 1858-1861 (1998).

Hayes, Matthew J., et al.; "Quantitative evaluation of photoplethysmographic artifact reduction for pulse oximetry," *SPIE*, vol. 3570, pp. 138-147 (Sep. 1998).

Edrich, Thomas, et al.; "Can the Blood Content of the Tissues be Determined Optically During Pulse Oximetry Without Knowledge of the Oxygen Saturation?—An In-Vitro Investigation," *Proceedings of the 20th Annual International conference of the IEEE Engineering in Medicine and Biology Society*, vol. 20, No. 6, pp. 3072-3075 (1998).

Hayes, Matthew J., et al.; "Artifact reduction in photoplethysmography," *Applied Optics*, vol. 37, No. 31, pp. 7437-7446 (Nov. 1998).

Such, Hans Olaf; "Optoelectronic Non-invasive Vascular Diagnostics Using multiple Wavelength and Imaging Approach," *Dissertation*, (1998).

Lutter, N., et al.; "Comparison of Different Evaluation Methods for a Multi-wavelength Pulse Oximeter," *Biomedizinische Technik*, vol. 43, (1998).

Ferrell, T.L., et al.; "Medical Telesensors," *SPIE*, vol. 3253, pp. 193-198 (1998).

Todd, Bryan, et al.; "The Identification of Peaks in Physiological Signals," *Computers and Biomedical Research*, vol. 32, pp. 322-335 (1999).

Rhee, Sokwoo, et al.; "Design of a Artifact-Free Wearable Plethysmographic Sensor," *Proceedings of the First joint BMES/EMBS Conference*, Oct. 13-16, 1999, Altanta, Georgia, p. 786.

Rohling, Roman, et al.; "Clinical Investigation of a New Combined Pulse Oximetry and Carbon Dioxide Tension Sensor in Adult Anaesthesia," *Journal o Clinical Monitoring and Computing*, vol. 15; pp. 23-27 (1999).

Ikeda, Kenji, et al.; "Improvement of Photo-Electric Plethysmograph Applying Newly Developed Opto-Electronic Devices," *IEEE Tencon*, pp. 1109-1112 (1999).

Kaestle, S.; "An Algorithm for Reliable Processing of Pulse Oximetry Signals Under strong Noise Conditions," *Dissertation Book*, Lubeck University, Germany (1999).

Seelbach-Göbel, Birgit, et al.; "The prediction of fetal acidosis by means of intrapartum fetal pulse oximetry," *Am J. Obstet. Gynecol.*, vol. 180, No. 1, Part 1, pp. 73-81 (1999).

Yang, Boo-Ho, et al.; "Development of the ring sensor for healthcare automation," *Robotics and Autonomous Systems*, vol. 30, pp. 273-281 (2000).

Rhee, Sokwoo, et al.; "Artifact-Resistant, Power-Efficient Design of Finger-Ring Plethysmographic Sensor—Part I: Design and Analysis," *Proceedings of the 22nd Annual EMBS International Conference*, Chicago, Illinois; Jul. 23-28, 2000; pp. 2792-2795.

Rhee, Sokwoo, et al.; "Artifact-Resistant, Power-Efficient Design of Finger-Ring Plethysmographic Sensor—Part II: Prototyping and Benchmarking," *Proceedings of the 22nd Annual EMBS International Conference*, Chicago, Illinois; Jul. 23-28, 2000; pp. 2796-2799.

Vicenzi, Martin N.; "Transesophageal versus surface pulse oximetry in intensive care unit patients," *Crit. Care Med.*; vol. 28, No. 7, pp. 2268-2270 (2000).

Goldman, Julian M.; "Masimo Signal Extraction Pulse Oximetry," *Journal of Clinical Monitoring and Computing*, vol. 16, pp. 475-483 (2000).

Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026,.

Nilsson, Lena, et al.; "Monitoring of Respiratory Rate in Postoperative Care Using a New Photoplethysmographic Technique," *Journal of Clinical Monitoring and Computing*, vol. 16, pp. 309-315 (2000).

Nijland, Mark J.M., et al.; "Assessment of fetal scalp oxygen saturation determination in the sheep by transmission pulse oximetry," *Am. J. Obstet Gynecol.*, vol. 183, No. 6, pp. 1549-1553 (Dec. 2000).

Edrich, Thomas, et al.; "Pulse Oximetry: An Improved In Vitro Model that Reduces Blood Flow-Related Artifacts," *IEEE Transactions on Biomedical Engineering*, vol. 47, No. 3, pp. 338-343 (Mar. 2000).

Schulz, Christian Eric; "Design of a Pulse Oximetry Sensor Housing Assembly," California State University Master's Thesis, *UMI Dissertation Services*, UMI No. 1401306, (May 2000) 63 pages.

Yao, Jianchu, et al.; "Design of a Plug-and-Play Pulse Oximeter," *Proceedings of the Second Joint EMBS/BMES Conference*, Houston, Texas, Oct. 23-26, 2002; pp. 1752-1753.

Aoyagi, T., et al.; "Pulse Oximeters: background, present and future," *Neonatal Care*, vol. 13, No. 7, pp. 21-27 (2000) (Article in Japanese—contains English summary of article).

Yokota, Nakaura, Takahashi, et al.; "Pilot Model of a Reflectance-Type Pulse Oximeter for Pre-hospital Evaluation," *Journal of the Japanese Society of Emergency Medicine*, Kanto Region, vol. 21, pp. 26-27 (2000) (Article in Japanese—contains English summary of article).

Kaestle, S.; "Determining Artefact Sensitivity of New Pulse Oximeters in Laboratory Using Signals Obtained from Patient," *Biomedizinische Technik*, vol. 45 (2000).

Cubeddu, Rinaldo, et al.; "Portable 8-channel time-resolved optical imager for functional studies of biological tissues," *Photon Migration, Optical Coherence Tomography, and Microscopy, Proceedings of SPIE*, vol. 4431, pp. 260-265 (2001).

Gisiger, P.A., et al.; "OxiCarbo®, a single sensor for the non-invasive measurement of arterial oxygen saturation and $CO_2$ partial pressure at the ear lobe," *Sensor and Actuators*, vol. B-76, pp. 527-530 (2001).

Cysewska-Sobusaik, Anna; "Metrological Problems With noninvasive Transillumination of Living Tissues," *Proceedings of SPIE*, vol. 4515, pp. 15-24 (2001).

Rhee, Sokwoo, et al.; "Artifact-Resistant, Power-Efficient Design of Finger-Ring Plethysmographic Sensor," *IEEE Transactions on Biomedical Engineering*, vol. 48, No. 7, pp. 795-805 (Jul. 2001).

Belal, Suliman Yousef, et al.; "A fuzzy system for detecting distorted plethysmogram pulses in neonates and paediatric patients," *Physiol. Meas.*, vol. 22, pp. 397-412 (2001).

Hayes, Matthew J., et al.; "A New Method for Pulse Oximetry Possessing Inherent Insensitivity to Artifact," *IEEE Transactions on Biomedical Engineering*, vol. 48, No. 4, pp. 452-461 (Apr. 2001).

Gosney, S., et al.; "An alternative position for the pulse oximeter probe," *Anaesthesia*, vol. 56, p. 493 (2001).

Silva, Sonnia Maria Lopez, et al.; "NIR transmittance pulse oximetry system with laser diodes," *Clinical Diagnostic Systems, Proceedings of SPIE*, vol. 4255, pp. 80-87 (2001).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Earthrowl-Gould, T., et al.; "Chest and abdominal surface motion measurement for continuous monitoring of respiratory function," *Proc. Instn Mech Engrs*, V215, Part H; pp. 515-520 (2001).

Gehring, Harmut, et al.; "The Effects of Motion Artifact and Low Perfusion on the Performance of a New Generation of Pulse Oximeters in Volunteers Undergoing Hypoxemia," *Respiratory Care*, Vo. 47, No. 1, pp. 48-60 (Jan. 2002).

Jopling, Michae W., et al.; "Issues in the Laboratory Evaluation of Pulse Oximeter Performance," *Anesth Analg*, vol. 94, pp. S62-S68 (2002).

Gostt, R., et al.; "Pulse Oximetry Artifact Recognition Algorithm for Computerized Anaesthetic Records," *Journal of Clinical Monitoring and Computing Abstracts*, p. 471 (2002).

Chan, K.W., et al.; "17.3: Adaptive Reduction of Motion Artifact from Photoplethysmographic Recordings using a Variable Step-Size LMS Filter," *IEEE*, pp. 1343-1346 (2002).

Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.

Yamaya, Yoshiki, et al.; "Validity of pulse oximetry during maximal exercise in normoxia, hypoxia, and hyperoxia," *J. Appl. Physiol.*, vol. 92, pp. 162-168 (2002).

Lutter, Norbert O., et al.; "False Alarm Rates of Three Third-Generation Pulse Oximeters in PACU, ICU and IABP Patients," *Anesth Analg*, vol. 94, pp. S69-S75 (2002).

Lutter, N., et al.; "Accuracy of Noninvasive Continuous Blood Pressure; Measurement Utilising the Pulse Transit Time," *Journal of clinical Monitoring and Computing*, vol. 17, Nos. 7-8, pp. 469 (2002).

Liu, Ying, et al.; "Sensor design of new type reflectance pulse oximetry," *Optics in Health Care and Biomedical Optics: Diagnostics and Treatment, Proceedings of SPIE*, vol. 4916, pp. 98-102 (2002).

Kyriacou, Panayiotis A., et al.; "Esophageal Pulse Oximetry Utilizing Reflectance Photoplethysmography," *IEEE Transactions on Biomedical Engineering*, vol. 49, No. 11, pp. 1360-1368 (Nov. 2002).

Kyriacou, P. A., et al.; "Investication of oesophageal photoplethysmographic signals and blood oxygen saturation measurements in cardiothoracic surgery patients," *Physiological Measurement*, vol. 23, No. 3, pp. 533-545 (Aug. 2002).

Tobata, H., et al.; "Study of Ambient Light Affecting Pulse Oximeter Probes," *Ikigaku (Medical Technology)*, vol. 71, No. 10, pp. 475-476 (2002) (Article in Japanese—contains English summary of article).

Irie, A., et al.; "Respiration Monitors—Pulse Oximeters," *Neonatal Care*, vol. 15, No. 12, pp. 78-83 (2002) (Article in Japanese—contains English summary of article).

Koga, I., et al.; "Sigmoid colonic reflectance pulse oximetry and tonometry in a porcine experimental hypoperfusion shock model," *Acta Anaesthesiol Scand*, vol. 46, pp. 1212-1216 (2002).

Shaltis, Phillip, et al.; "Implementation and Validation of a Power-Efficient, High-Speed Modulation Design for Wireless Oxygen Saturation Measurement Systems," *IEEE*, pp. 193-194 (2002).

Warren, Steve, et al.; "Wearable Sensors and Component-Based Design for Home Health Care," *Proceedings of the Second Joint EMBS/BMES Conference*, Houston, Texas; Oct. 23-26, 2002; pp. 1871-1872.

Ericson, M.N., et al.; "In vivo application of a minimally invasive oximetry based perfusion sensor," *Proceedings of the Second Joint EMBS/BMES Conference*, Houston, Texas; Oct. 23-26, 2002; pp. 1789-1790.

Yoon, Gilwon, et al.; Multiple diagnosis based on Photoplethysmography: hematocrib, SpO2, pulse and respiration, *Optics in Health Care and Biomedical optics: Diagnostics and Treatment; Proceedings of the SPIE*, vol. 4916; pp. 185-188 (2002).

Hase, Kentaro, et al.; "Continuous Measurement of Blood Oxygen Pressure Using a Fiber Optic Sensor Based on Phosphorescense Quenching," *Proceedings of the Second Joint EMBS/BMES Conference, Houston*, Texas; Oct. 23-26, 2002, pp. 1777-1778.

Pothisarn, W., et al.; "A non-invasive hemoglobin measurement based pulse oximetry," *Optics in Health Care and Biomedical Optics: Diagnostics and Treatment; Proceedings of SPIE*, vol. 4916; pp. 498-504 (2002).

Tremper, K.K.; "A Second Generation Technique for Evaluating Accuracy and Reliability of Second Generation Pulse Oximeters," *Journal of Clinical Monitoring and Computing*, vol. 16, pp. 473-474 (2002).

Silva, Sonnia Maria Lopez, et al.; "Near-infrared transmittance pulse oximetry with laser diodes," *Journal of Biomedical Optics*, vol. 8, No. 3, pp. 525-533 (Jul. 2003).

Cyrill, D., et al.; "Adaptive Comb Filter for Quasi-Periodic Physiologic Signals," *Proceedings of the 25th Annual International Conference of the IEEE EMBS*, Cancun, Mexico, Sep. 17-21, 2003; pp. 2439-2442.

Matthews, Nora S. et al.; "An evaluation of pulse oximeters in dogs, cats and horses," *Veterinary Anaesthesia and Analgesia*, vol. 30, pp. 3-14 (2003).

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

Aoyagi, Takuo; "Pulse oximetry: its invention, theory, and future," *Journal of Anesthesia*, vol. 17, pp. 259-266 (2003).

Avidan, A.; "Pulse oximeter ear probe," *Anaesthesia*, vol. 58, pp. 726 (2003).

Lee, C.M., et al.; "Reduction of motion artifacts from photoplethysmographic recordings using wavelet denoising approach," *IEEE EMBS Asian-Pacific Conference on Biomedical Engineering*, Oct. 20-22, 2003; pp. 194-195.

Mendelson, Y., et al.; "Measurement Site and Photodetector Size Considerations in Optimizing Power Consumption of a Wearable Reflectance Pulse Oximeter," *Proceedings of the 25th Annual International conference of the IEEE EMBS*, Cancun, Mexico, Sep. 17-21, 2003; pp. 3016-3019.

ltoh, K., et al.; "Pulse Oximeter," *Toyaku Zasshi* (Toyaku Journal), vol. 25, No. 8, pp. 50-54 (2003) (Article in Japanese—contains English summary of article).

Matsui, A., et al.; "Pulse Oximeter," *Neonatal Care* vol. 16, No. 3, pp. 38-45 (2003) (Article in Japanese —contains English summary of article).

Nakagawa, M., et al.; "Oxygen Saturation Monitor," *Neonatal Monitoring*, vol. 26, No. 5, pp. 536-539 (2003) (Article in Japanese—contains English summary of article).

Kubota, H., et al.; "Simultaneous Monitoring of PtcCO2 and SpO2 using a Miniature earlobe sensor," *Jinko Kokyo* (*Aritificial Respiration*), vol. 20, No. 1, pp. 24-29 (2003).

Lebak, J.W., et al.; "Implementation of a Standards-Based Pulse Oximeter on a Wearable, Embedded Platform," *Proceeding of the 25th Annual International Conference of the IEEE EMBS*, Cancun, Mexico, Sep. 17-21, 2003; pp. 3196-3198.

Nag, L., et al.; "Wearable Sensor System for Wireless State-of-Health Determination in Cattle," *Proceeding of the 25th Annual International Conference of the IEEE EMBS*, Cancun, Mexico, Sep. 17-21, 2003; pp. 3012-3015.

Östmark, Åke, et al.; "Mobile Medical Applications Made Feasible Through Use of EIS Platforms," *IMTC—Instrumentation and Measurement Technology Conference*, Vail, Colorado; May 20-22, 2003; pp. 292-295.

Warren, Steve, et al.; "A Distributed Infrastructure for Veterinary Telemedicine," *Proceedings of the 25th Annual International Conference of the IEEE EMBS*, Cancun, Mexico; Sep. 17-21, 2003; pp. 1394-1397.

Pujary, C., et al.; "Photodetector Size Considerations in the Design of a Noninvasive Reflectance Pulse Oximeter for Telemedicine Applications," *IEEE*, pp. 148-149 (2003).

A. Johansson; "Neural network for photoplethysmographic respiratory rate monitoring," *Medical & Biological Engineering & Computing*, vol. 41, pp. 242-248 (2003).

Reuss, James L.; "Factors Influencing Fetal Pulse Oximetry Performance," *Journal of clinical Monitoring and Computing*, vol. 18, pp. 13-14 (2004).

Mannheimer, Paul D., et al.; "The influence of Larger Subcutaneous Blood Vessels on Pulse Oximetry," *Journal of clinical Monitoring and Computing* vol. 18, pp. 179-188 (2004).

Wendelken, Suzanne, et al.; "The Feasibility of Using a Forehead Reflectance Pulse Oximeter for Automated Remote Triage," *IEEE*, pp. 180-181 (2004).

Lopez-Silva, S.M., et al.; "Transmittance Photoplethysmography and Pulse Oximetry With Near Infrared Laser Diodes," *IMTC*

*2004—Instrumentation and Measurement Technology Conference*, Como, Italy, May 18-20, 2004; pp. 718-723.

Sugino, Shigekzau, et al.; "Forehead is as sensitive as finger pulse oximetry during general anesthesia," *Can J. Anesth.; General Anesthesia*, vol. 51, No. 5; pp. 432-436 (2004).

Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).

Jovanov, E., et al.; "Reconfigurable intelligent Sensors for Health Monitoring: A case Study of Pulse Oximeter Sensor," *Proceedings o the 26th Annual International conference of the IEEE EMBS*, San Francisco, California, Sep. 1-5, 2004, pp. 4759-4762.

Kocher, Serge, et al.; "Performance of a Digital $PCO_2/SPO_2$ Ear Sensor," *Journal of Clinical Monitoring and Computing*, vol. 18, pp. 75-59 (2004).

Yao, Jianchu, et al.; "A Novel Algorithm to Separate Motion Artifacts from Photoplethysmographic Signals Obtained With a Reflectance Pulse Oximeter," *Proceedings of the 26th Annual International conference of the IEEE EMBS*, San Francisco, California, Sep. 1-5, 2004; pp. 2153-2156.

Nuhr, M., et al.: "Forehead $SpO_2$ monitoring compared to finger $SpO_2$ recording in emergency transport," *Anaesthesia*, vol. 59, pp. 390-393 (2004).

Johnston, William S., et al.; "Effects of Motion Artifacts on helmet-Mounted Pulse Oximeter Sensors," 2 pgs. (2004).

Branche, Paul C., et al.; "Measurement Reproducibility and Sensor Placement Considerations in Designing a Wearable Pulse Oximeter for Military Applications," 2 pgs. (2004).

Kocher, Serge, et al.; "Performance of a Digital $PCO_2/SPO_2$ Ear Sensor," *Journal of Clinical Monitoring and Computing*, vol. 18, pp. 75-79 (2004).

Heuss, Ludwig T., et al.; "Combined Pulse Oximetry / Cutaneous Carbon dioxide Tension Monitoring During Colonoscopies: Pilot study with a Smart Ear Clip," *Digestion*, vol. 70, pp. 152-158 (2004).

Matsuzawa, Y., et al.; "Pulse Oximeter," *Home Care Medicine*, pp. 42-45 (Jul. 2004); (Article in Japanese—contains English summary of article).

Crespi, F., et al.; "Near infrared oxymeter prototype for non-invasive analysis of rat brain oxygenation," *Optical Sensing, Proceedings of SPIE*, vol. 5459, pp. 38-45 (2004).

Johnston, W.S., et al.; "Extracting Breathing Rate Infromation from a Wearable Reflectance Pulse Oximeter Sensor," *Proceedings of the 26th Annual International conference of the IEEE EMBS*, San Francisco, California; Sep. 1-5, 2004; pp. 5388-5391.

Spigulis, Janis, et al.; "Optical multi-channel sensing of skin blood pulsations," *Optical Sensing, Proceedings of SPIE*, vol. 5459, pp. 46-53 (2004).

Yan, Yong-sheng, et al.; "Reduction of motion artifact in pulse oximetry by smoothed pseudo Wigner-Ville distribution," *Journal of NeuroEngineering and Rehabilitation*, vol. 2, No. 3 (9 pages) (Mar. 2005).

Urquhart, C., et al.; "Ear probe pulse oximeters and neonates," *Anaesthesia*, vol. 60, p. 294 (2005).

\* cited by examiner

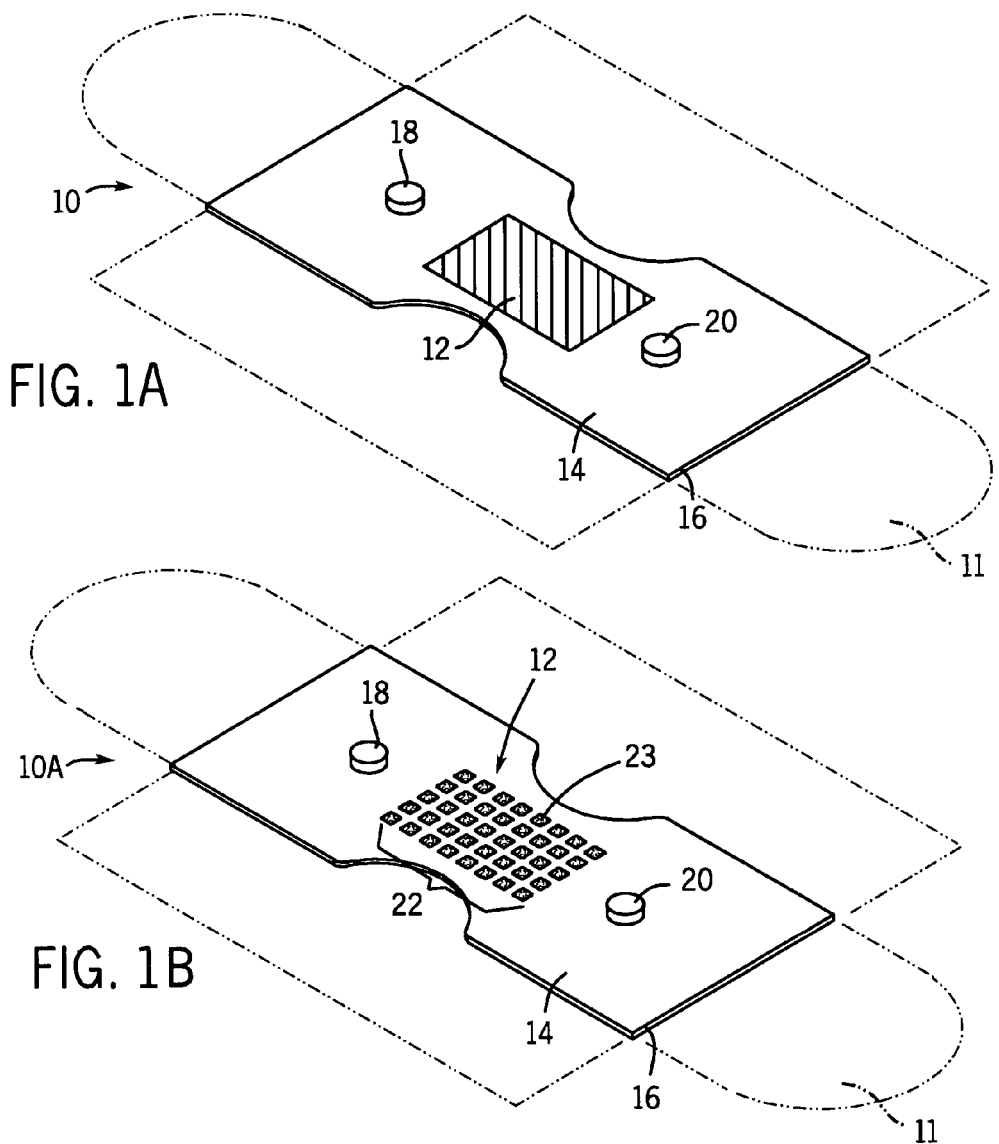
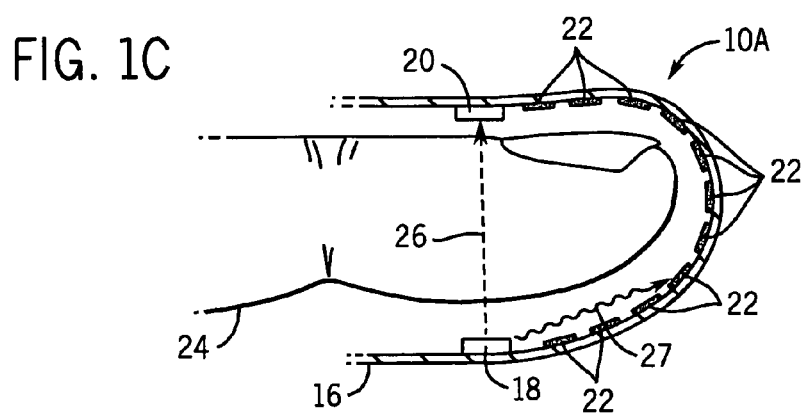

MEDICAL SENSOR AND TECHNIQUE FOR USING THE SAME

CROSS REFERENCE TO RELATED APPLICATIONS

This application is a continuation of prior U.S. application Ser. No. 11/241,508, filed Sep. 29, 2005, the specification of which is incorporated by reference in its entirety.

BACKGROUND OF THE INVENTION

1. Field of the Invention

The present invention relates generally to medical devices and, more particularly, to sensors used for sensing physiological parameters of a patient.

2. Description of the Related Art

This section is intended to introduce the reader to various aspects of art that may be related to certain aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such characteristics of a patient. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry measures various blood flow characteristics, such as the blood-oxygen saturation of hemoglobin in arterial blood, the volume of individual blood pulsations supplying the tissue, and/or the rate of blood pulsations corresponding to each heartbeat of a patient. In fact, the "pulse" in pulse oximetry refers to the time varying amount of arterial blood in the tissue during each cardiac cycle.

Pulse oximeters typically utilize a non-invasive sensor that emits light into a patient's tissue and that photoelectrically detects the absorption and/or scattering of the transmitted light in such tissue. One or more of the above physiological characteristics may then be calculated based upon the amount of light absorbed or scattered. More specifically, the light passed through the tissue is typically selected to be of one or more wavelengths that may be absorbed or scattered by the blood in an amount related to the amount of a blood constituent present in the blood. The amount of light absorbed and/or scattered may then be used to estimate the amount of the blood constituent in the tissue using various algorithms.

The pulse oximetry measurement depends in part on the assumption that the contribution of light that has not passed through a patient's tissue is negligible. However, outside light may leak into a sensor, causing detection of light that is not related to the amount of blood constituent present in the blood. Additionally, light from a sensor's emitter may be reflected around the exterior of the tissue and may impinge the detector without traveling first through the tissue. These light sources may cause measurement variations that do not relate to amount of the blood constituent.

Some outside light infiltration into the sensor may be avoided by fitting the sensor snugly against the patient's tissue. However, such a conforming fit may be difficult to achieve over a range of patient physiologies without adjustment or excessive attention on the part of medical personnel. Additionally, an overly tight fit may cause local exsanguination of the tissue around the sensor. Exsanguinated tissue, which is devoid of blood, may shunt the sensor light through the tissue, which may also result in increased measurement errors.

SUMMARY

Certain aspects commensurate in scope with the originally claimed invention are set forth below. It should be understood that these aspects are presented merely to provide the reader with a brief summary of certain forms that the invention might take and that these aspects are not intended to limit the scope of the invention. Indeed, the invention may encompass a variety of aspects that may not be set forth below.

There is provided a sensor that includes: a sensor body; an emitter disposed on the sensor body, wherein the emitter is adapted to transmit light into tissue; a detector disposed on the sensor body, wherein the detector is adapted to detect the light; and a patterned region disposed on a tissue-contacting surface of the sensor body between the emitter and the detector, the patterned region being configured to at least absorb, refract, redirect, or diffract the light.

There is also provided a pulse oximetry system that includes: a pulse oximetry monitor; and a pulse oximetry sensor adapted to be operatively coupled to the monitor, the sensor comprising: a sensor body; an emitter disposed on the sensor body, wherein the emitter is adapted to transmit light into tissue; a detector disposed on the sensor body, wherein the detector is adapted to detect the light; and a patterned region disposed on a tissue-contacting surface of the sensor body between the emitter and the detector, the patterned region being configured to at least absorb, refract, redirect, or diffract the light.

There is also provided a method that includes: delivering a first light through a patient's tissue; detecting the first light delivered through the tissue; and redirecting a second light that does not propagate through the tissue away from the detector with a patterned region.

There is also provided a method that includes: providing a sensor body; providing an emitter adapted to transmit light into tissue; providing a detector adapted to detect the light; and providing a patterned region on a tissue-contacting surface of the sensor body between the emitter and the detector, the patterned region being configured to at least absorb, refract, redirect, or diffract the light.

There is also provided a sensor that includes: a sensor body adapted to operate in a transmission mode; an emitter disposed on the sensor body, wherein the emitter is adapted to deliver a first light into a tissue; a detector disposed on the sensor body, wherein the detector is adapted to detect the first light; and at least one protrusion disposed on a tissue-contacting surface of the sensor body, wherein the at least one protrusion is adapted to reduce the amount of a second light impinging the detector at an incident angle substantially not in-line with an imaginary axis connecting the emitter and the detector.

There is also provided a pulse oximetry system that includes: a pulse oximetry monitor; and a pulse oximetry sensor adapted to be operatively coupled to the monitor, the sensor comprising: a sensor body adapted to operate in a transmission mode; an emitter disposed on the sensor body, wherein the emitter is adapted to deliver a first light into a tissue; a detector disposed on the sensor body, wherein the detector is adapted to detect the first light; and at least one protrusion disposed on a tissue-contacting surface of the sensor body, wherein the at least one protrusion is adapted to reduce the amount of a second light impinging the detector at an incident angle substantially not in-line with an imaginary axis connecting the emitter and the detector.

There is also provided a method that includes: delivering a first light through a patient's tissue; detecting the first light delivered through the tissue; and redirecting a second light that does not propagate through the tissue away from the detector with a protruding feature.

There is also provided a method that includes: providing a transmission-type sensor body; providing an emitter adapted to transmit a first light into tissue; providing a detector adapted to detect the first light; providing at least one protrusion disposed on a tissue-contacting surface of the sensor body, wherein the at least one protrusion is adapted to reduce the amount of a second light impinging the detector at an incident angle substantially not in-line with an imaginary axis connecting the emitter and the detector.

There is also provided a sensor that includes: a sensor body adapted to operate in a reflectance mode; an emitter disposed on the sensor body, wherein the emitter is adapted to deliver a first light into a tissue; a detector disposed on the sensor body, wherein the detector is adapted to detect the first light; and at least one protrusion disposed on a tissue-contacting surface of the sensor body, wherein the at least one protrusion is adapted to reduce the amount of a second light impinging the detector at an incident angle substantially in-line with an imaginary axis connecting the emitter and the detector.

There is also provided a pulse oximetry system that includes: a pulse oximetry monitor; and a pulse oximetry sensor adapted to be operatively coupled to the monitor, the sensor comprising: a sensor body adapted to operate in a reflectance mode; an emitter disposed on the sensor body, wherein the emitter is adapted to deliver a first light into a tissue; a detector disposed on the sensor body, wherein the detector is adapted to detect the first light; and at least one protrusion disposed on a tissue-contacting surface of the sensor body, wherein the at least one protrusion is adapted to reduce the amount of a second light impinging the detector at an incident angle substantially in-line with an imaginary axis connecting the emitter and the detector.

There is also provided a method that includes: providing a sensor body; providing an emitter adapted to transmit a first light into tissue; providing a detector adapted to detect the first light; and providing at least one protrusion adapted to reduce the amount of a second light impinging the detector disposed on a tissue-contacting surface of the sensor body, wherein the second light has an incident angle substantially in-line with an imaginary axis connecting the emitter and the detector.

There is also provided a sensor that includes: a sensor body; an emitter disposed on the sensor body, wherein the emitter is adapted to transmit a light into tissue; a detector disposed on the sensor body, wherein the detector is adapted to detect the light; and a light diffracting material disposed on a tissue-contacting surface of the sensor body.

BRIEF DESCRIPTION OF THE DRAWINGS

Advantages of the invention may become apparent upon reading the following detailed description and upon reference to the drawings in which:

FIG. 1A illustrates a perspective view of an embodiment of an exemplary bandage-style sensor with a patterned region in accordance with the present invention;

FIG. 1B illustrates a perspective view of the sensor of FIG. 1A with a checkerboard patterned region;

FIG. 1C illustrates a cross-sectional view of the sensor of FIG. 1B applied to a patient's digit;

DETAILED DESCRIPTION OF SPECIFIC EMBODIMENTS

Figure 2:
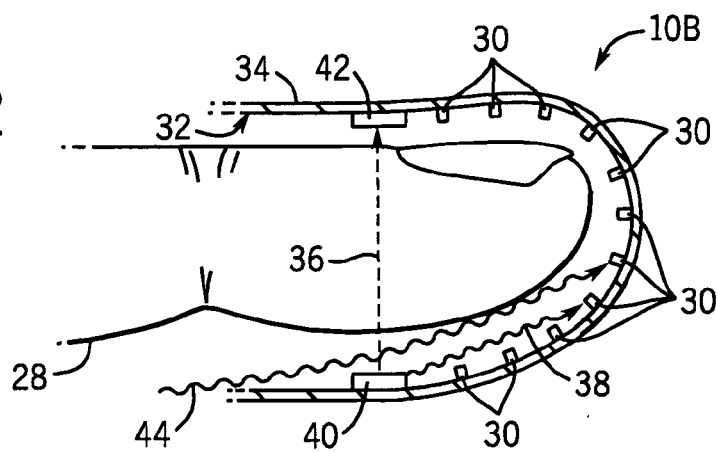
FIG. 2 illustrates a cross-sectional view of an exemplary sensor with protruding features applied to a patient's digit.

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

It is desirable to eliminate, reduce, or account for the possible influence of light sources which may cause variability in pulse oximetry measurements. In accordance with the present techniques, pulse oximetry sensors are provided that reduce the amount of outside light that impinges the detecting elements of a sensor. Such sensors also reduce the amount of "shunted" light, i.e., light originating from light emitting elements of the sensor that impinges the detecting elements of a sensor without first passing through tissue. Sensors according to the present techniques incorporate surface features on or near the tissue-contacting surface of the sensor, such as protruding elements or printed patterns, to influence the path of light from the undesired light sources and to direct such light away from the detecting elements of the sensor. Such sensors may absorb, refract, or diffract the light originating from these undesired light sources before such light can impinge the detecting elements of the sensor.

Pulse oximetry sensors are typically placed on a patient in a location that is normally perfused with arterial blood to facilitate measurement of the desired blood characteristics, such as arterial oxygen saturation measurement ($SpO_2$). The most common sensor sites include a patient's fingertips, toes, earlobes, or forehead. Regardless of the placement of a sensor 10 used for pulse oximetry, the reliability of the pulse oximetry measurement is related to the accurate detection of transmitted light that has passed through the perfused tissue and that has not been supplemented by undesired light sources. Such supplementation and/or modulation of the light transmitted by the sensor can cause variability in the resulting pulse oximetry measurements. The contribution of ambient or shunted light may adversely affect the measurement of the particular blood constituent, such as $SpO_2$.

In many cases, light from undesired light sources propagates along an optical path that is distinguishable from the optical path of the emitted light that is related to a blood constituent. In a transmission-type sensor, the sensor's emitter and detector lie on opposing sides of the tissue when the sensor is applied to a patient. The optical path of the signal light, which is light originating from the emitter that properly passes through perfused tissue, is substantially in-line with an imaginary axis connecting the emitter and the detector. For reflectance-type sensors, the optical path of the emitted signal light is somewhat more complicated, as the light first enters the perfused tissue and then is scattered back to the detector. In both transmission-type and reflectance-type sensors, shunted light and ambient light generally propagate at angles substantially off-axis from the optical path of the signal light.

The exemplary sensors discussed below have surface features that act to divert shunted or ambient light away from the light detecting elements of a sensor. In certain embodiments, those features may be patterns or designs. More specifically, FIG. 1A illustrates a perspective view of an exemplary bandage-style sensor 10 having a generic patterned region 12 disposed on a tissue-contacting surface 14 of the sensor body 16. As one with skill in the art understands, the tissue-contacting surface 14 of the sensor body 16 may be actually touching a patient's tissue, or may be almost touching the patient's tissue, depending on the closeness of the sensor's 10 fit. As depicted, the patterned region 12 is disposed in the region between the emitter 18 and the detector 20. The patterned region 12 may include a material that absorbs, refracts, or diffracts light. The sensor 10 may be applied to a patient's tissue with adhesives bandages 11.

For example, FIG. 1B illustrates a perspective view of the sensor 10A having a checkerboard pattern 22 disposed on a tissue-contacting surface of the sensor body. As depicted, the checkerboard is an alternating pattern of a light absorbing material 23. The material surrounding the portions of light absorbing material 23 may be the material from which the sensor body 16 is constructed.

FIG. 1C depicts a cross-sectional view of the sensor 10A with a checkerboard pattern 22 applied to a patient's digit 24. The optical path of signal light originating from the emitter is substantially in-line with an imaginary axis 26 connecting the emitter 18 and the detector 20. A small percentage of the light emitted by the emitter 18 may not enter the perfused digit 24. Instead, this light may be shunted around the space between the digit 24 and the sensor body 16. The shunted light, depicted by wavy arrow 27, impinges the light absorbing material in the checkerboard pattern 22, which absorbs the light, thus preventing it from reflecting around the gap between the sensor body 16 and the digit 24 to impinge the detector 20. It should be understood that the gap between the sensor body 16 and the digit 24 may be microscopic in scale for a sensor body 16 that conforms closely to the digit 24. Further, the gap may be discontinuous when interrupted by points where the sensor body 16 is touching the digit 24. The checkerboard pattern 22 reduces the overall reflectivity of the sensor body 16 on the tissue-contacting surface 14, which may reduce the amount of shunted light that reaches the detector 20. The checkerboard pattern 22, or other suitable pattern or design, may easily be applied to the sensor body 16 with inks or dyes, and is thus a low-cost modification which may reduce measurement errors. In certain embodiments, the patterned region 12 does not protrude from the sensor body 16. However, in other embodiments, as depicted in FIG. 1C, the checkerboard pattern may be laminated onto the sensor body 16 so that it protrudes slightly from the sensor body 16.

A patterned region 12 may include a first material and a second material. The first material may be the material from which the sensor body is constructed. The second material may be a light absorbing, light refracting, or light diffracting material, or a combination thereof. The patterned region 12 may include more than two materials, and may also include materials that are intermediate in their ability to absorb, refract, or diffract light. The patterned region 12 may also include an anti-reflective material. In certain embodiments, the patterned region 12 may be a single material that is applied in varying intensity or concentration to the sensor body. For example, a checkerboard pattern 22 may be an alternating pattern of black ink and gray ink.

Additionally, the patterned region 12 may be a regular pattern, such as a checkerboard pattern 22, a concentric circles pattern, or a striped pattern. The patterned region 12 may also be an irregular pattern that is customized to provide redirection of light in specific areas of the sensor 10 which ambient or shunted light may be most likely to impinge. The patterned region 12 may be microscopic in scale, or it may be visible to the unaided eye. In certain embodiments, it is envisioned that the sensor body 16 is impregnated with the inks, dyes, or paints used to make the patterned region 12.

Generally, it is envisioned that the patterned region 12 will cover at least 1% of the surface area of the tissue-contacting surface 14 of a sensor body 16. The tissue contacting surface 14 may include only the sensor body 16 or may also include the combined total tissue-contacting area of the sensor body 16 and of the adhesive bandages 11. In certain embodiments, the patterned region 12 will cover 10-50% of the surface area of the tissue-contacting surface 14 of a sensor body 16. In other embodiments, the patterned region may cover at least 75% of the surface area of a tissue-contacting surface 14 of a sensor body 16. Generally, it is contemplated that in addition to disposing a patterned region between an emitter 18 and detector 20, it may be advantageous to dispose a patterned region near any edges of the sensor 10A that may allow ambient light to infiltrate into a sensor's 10 interior.

Furthermore, the patterned region 12 may have three-dimensional protruding surface features that function to divert ambient or shunted light away from the light detecting elements of the sensor. FIG. 2 depicts a cross-sectional view of a transmission-type sensor 10B applied to a patient digit 28. The sensor 10B has protruding surface features 30 disposed on the tissue-contacting surface 32 of the sensor body 34. The protruding surface features 30 may be integrally formed or molded with the sensor body 34, or they may be applied to the tissue-contacting surface 32 of the sensor body 34 adhesively or otherwise. The protruding surface features 30 may be small-scale protruding features. Generally, small-scale protruding features as described herein are contemplated to protrude less than about 0.001 mm from the tissue-contacting surface 32 of the sensor body 34. In certain embodiments, the small-scale protruding features are not visible to the unaided eye. Alternatively, the protruding surface features 30 may be large-scale protruding features. Generally, large-scale protruding features as described herein are clearly visible to the unaided eye, and they are contemplated to protrude at least about 0.001 mm from the tissue-contacting surface 32 of the sensor body 34. In certain embodiments, the large-scale protruding features protrude about 0.001 mm to about 1 mm from the tissue-contacting surface 32 of the sensor body 34. The protruding features may be sized and shaped to avoid substantially interfering with a suitably conforming sensor fit.

Turning to FIG. 2 in greater detail, the optical path of signal light originating from the emitter is substantially in-line with an imaginary axis 36 connecting the emitter 40 and the detector 42. However, a small percentage of the light from the emitter, illustrated by wavy arrow 38, may not pass through the perfused tissue, but instead may be reflected off the surface of the digit 28 and shunted around the gap between the digit 28 and the tissue-contacting surface 32 of the sensor body 34. As the shunted light, wavy arrow 38, propagates along its optical path, it impinges the protruding features 30 on the tissue-contacting surface 32. The protruding features 30 change the optical path of the shunted light, reducing the amount of shunted light that impinges on the detector 42.

The sensor 10B may also reduce the contribution of outside light sources to pulse oximetry measurements. Ambient light, depicted as wavy arrow 44, is shown leaking into the sensor 10B and impinging on the protruding features 30. The protruding features 30 reduce the amount of ambient light that reaches the detector 42. As the protruding features 30 are not in-line with the imaginary axis 36, the optical path of the light transmitted by the emitter 40 into the digit 28 is not substantially affected by the protruding features 30. Hence, the contribution of shunted light and ambient to the light received by the detector 42 is reduced, thus improving the signal to noise ratio.

Figure 3:
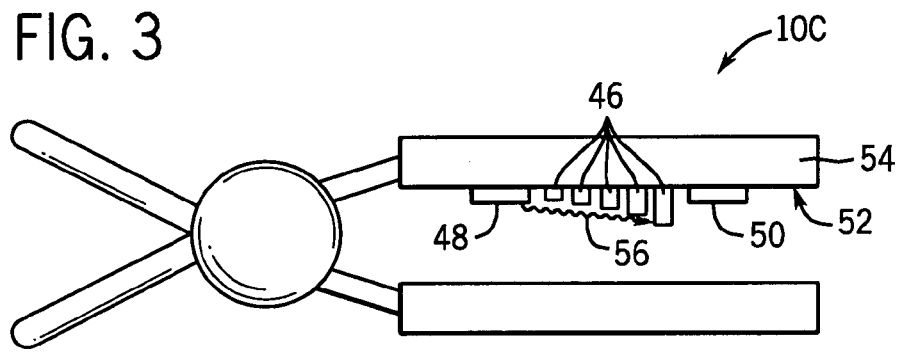
FIG. 3 illustrates a cross-sectional view of an exemplary reflectance sensor with protruding features.

In certain embodiments, it may be advantageous to use large-scale protruding features, as described above, to redirect light from undesired light sources away from a detector. For example, when using reflectance type sensors, it may be useful to block light that may shunt directly between the emitter and detector of such a sensor. FIG. 3 illustrates a cross-sectional view of a reflectance-type sensor 10C with large-scale protruding features 46 adapted to block light from the emitter 48 that shunts directly to the detector 50 without first passing through perfused tissue. In certain embodiments, a light shunt between the emitter 48 and the detector 50 may be addressed by placing one or more large-scale protruding features 46 on the tissue-contacting surface 52 of the sensor body 54 between the emitter 48 and the detector 50. As the emitted light, depicted by wavy arrow 56, strikes the side of the large-scale protruding features 46, it will be redirected away from the detector 50. As depicted, the large-scale protruding features 46 are heterogeneous in size, and they are arranged such that the protruding features 46 closest to the detector 50 protrude the most from the sensor body 54. In certain embodiments, at least one of the large-scale surface features 46 should protrude from the tissue-contacting surface 52 of the sensor body 54 at least as far as the detector 50 protrudes from the tissue-contacting surface 52 of the sensor body 54.

Figure 4A:
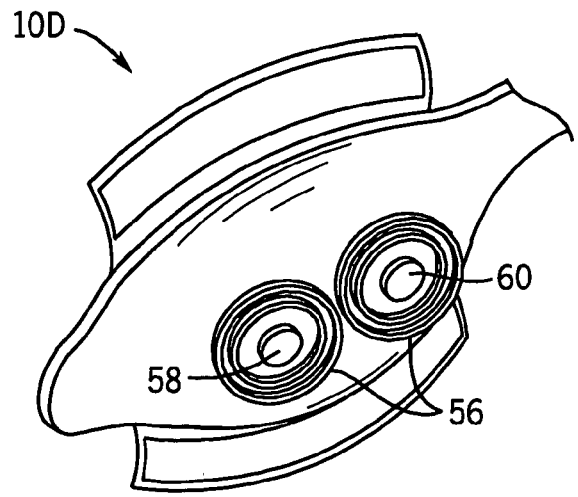
FIG. 4A illustrates a perspective view of an embodiment of an exemplary bandage-style sensor with protruding features in a concentric pattern in accordance with the present invention.
Figure 4B:
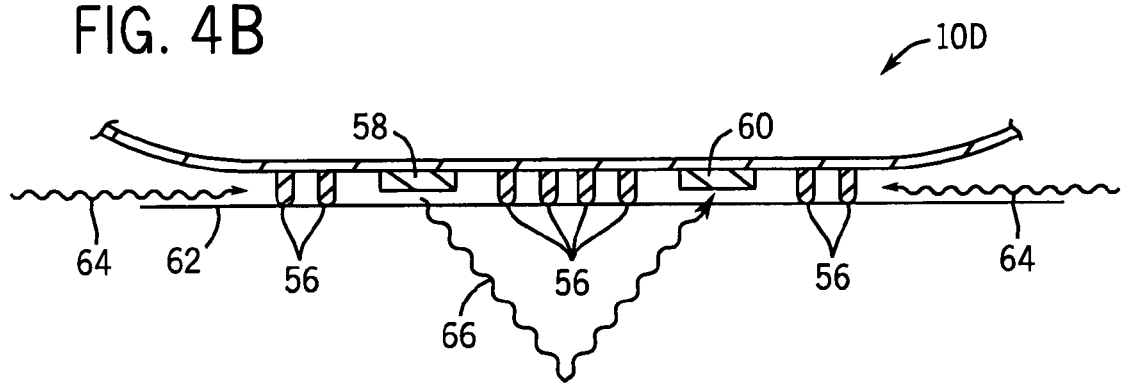
FIG. 4B illustrates a cross-sectional view of the sensor of FIG. 4A applied to a patient's forehead.

In another embodiment, shown in FIGS. 4A and 4B, large-scale protruding features may be arranged to form a pattern. FIG. 4A is a perspective view of a forehead sensor 10D with protruding features 56 arranged in concentric circles that substantially encircle an emitter 58 and a detector 60. FIG. 4B is a cross-sectional view of the sensor 10D applied to a patient's forehead. Such an arrangement of protruding features 56 may be advantageous in forming a seal with the tissue 62, thus creating a barrier against any ambient light or shunted light that may leak into the sensor 10D. The ambient light, depicted by wavy arrows 64, impinges the protruding features and is prevented from reaching the detector 60. The optical path of the signal light, depicted by wavy arrow 66, is substantially unaffected by the protruding features 56.

In general, when shunted or ambient light impinges the protruding features, as described above, its optical path is altered and redirected away from the detector of a sensor 10. This may be accomplished in a variety of ways, as seen in FIGS. 5A-D, which depict cross-sectional views of exemplary sensor bodies with protruding features dispersed in the patterned area 12. It should be understood that any of the protruding features described below in FIGS. 5A-D may large-scale or small-scale, and they may be used alone or in combination with one another on any suitable sensor.

Figure 5A:
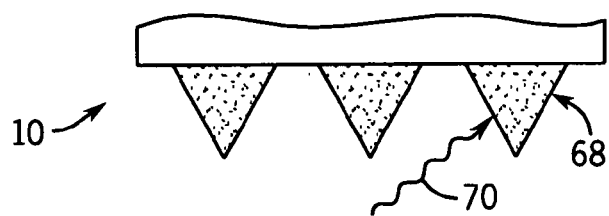
FIG. 5A illustrates a cross-sectional view of a region of an exemplary sensor with light absorbing protruding features in accordance with the present invention.
Figure 5B:
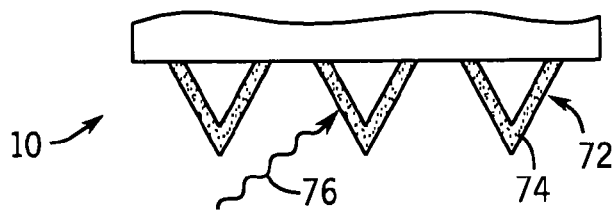
FIG. 5B illustrates a cross-sectional view of a region of an exemplary sensor with protruding features with a light absorbing coating in accordance with the present invention.
Figure 5C:
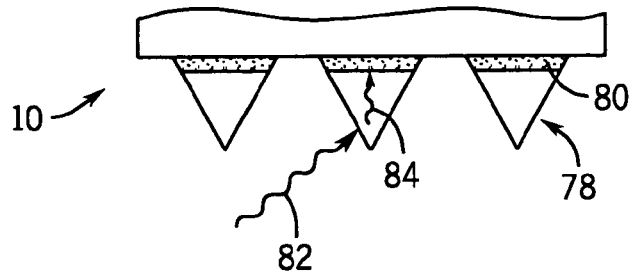
FIG. 5C illustrates a cross-sectional view of a region of an exemplary sensor with light refracting protruding features with a light absorbing backing in accordance with the present invention.

For example, as depicted in FIG. 5A, protruding features 68 may be made of a light-absorbing material. The impinging light, depicted as wavy arrow 70, is refracted into the bulk of the light-absorbing material where it is absorbed. In another embodiment, as seen in FIG. 5B, protruding features 72 may have a light-absorbing coating 74. The impinging light, depicted by wavy arrow 76, is absorbed as it contacts the light-absorbing coating 74 of the protruding features 72. In another embodiment, shown in FIG. 5C, protruding features 78 may be made of a substantially optically refractive material with an absorptive backing 80. The light, depicted by wavy arrow 82, is refracted into the refractive material of the protruding features 78, and the refracted light, depicted by wavy arrow 84, is absorbed by the absorptive backing 80.

Figure 5D:
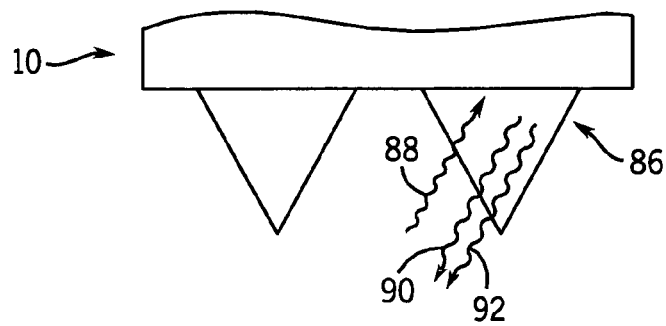
FIG. 5D illustrates a cross-sectional view of a region of an exemplary sensor with light diffracting protruding features in accordance with the present invention.

Alternatively, in another embodiment, shown in FIG. 5D, light from undesired light sources may be directed away from the detector through diffraction. In such an embodiment, protruding features 86 may be made of a diffracting material. For example, the diffracting material may be an interference grating material. As the impinging light, depicted by wavy arrow 88, impinges the protruding features 86, it is diffracted into destructively interfering beams, depicted by wavy arrows 90 and 92, that substantially cancel each other out. It is contemplated that the diffracting material may be adapted to selectively interfere with at least certain wavelengths. Thus, all or certain wavelengths of the impinging light may be prevented from reaching a detector.

Figure 6:
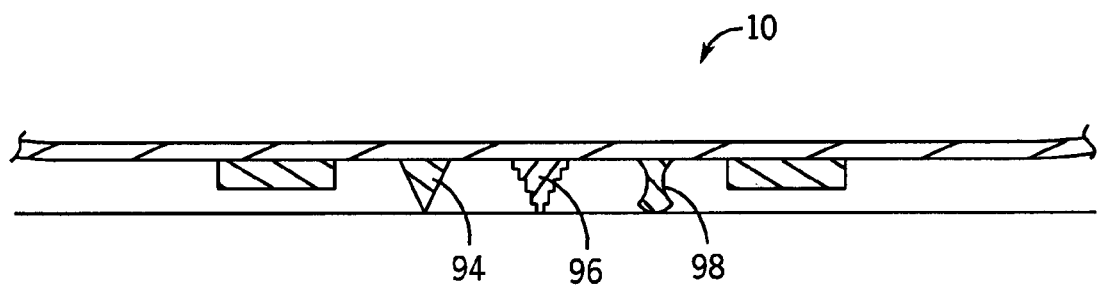
FIG. 6 illustrates exemplary protruding features for use with a sensor in accordance with the present invention.

As described above, it may be advantageous to refract a beam of light when it impinges a protruding feature as described herein. Ambient light or shunted light may impinge a protruding feature after propagating through air in the gap between the tissue and the sensor body. Alternatively, if the protruding feature is pressed tightly against the tissue, the light may travel through the cutaneous layer of the tissue to impinge the protruding feature. Light that impinges a protruding feature at an incident angle not normal, i.e., not 90 degrees, to the interface of the protruding feature with the air or tissue and the protruding feature will tend to be refracted. Thus, the protruding features may be shaped to promote light refraction. For example, as shown in FIG. 6, the protruding feature may have a generally sawtooth shape 94, which may be nonorthogonal to incident light leaking in. In another embodiment, a protruding feature 96 may have a complex profile in order to present a variety of possible interfaces to impinging light. Alternatively, a protruding feature 98 may have a curved profile to promote refraction. In certain embodiments, it is contemplated that the protruding features may incorporate a patterned region, as described herein, on their surfaces.

Figure 7:
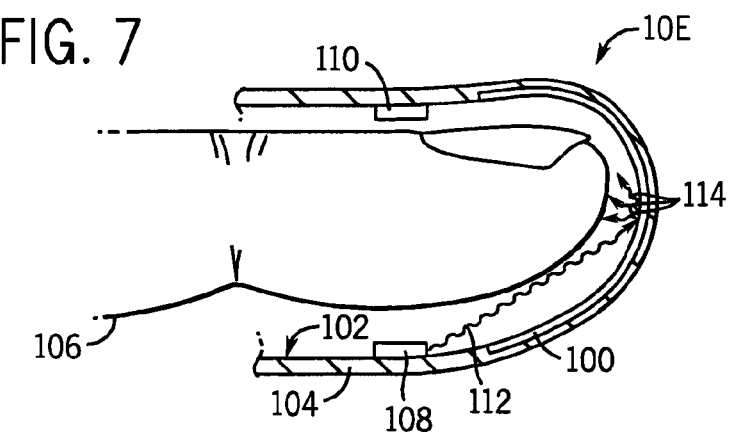
FIG. 7 illustrates a cross-sectional view of an exemplary sensor with a light diffracting material in accordance with the present invention.

As described above in FIG. 5D, materials with light diffracting properties may direct light from undesired light sources away from the detecting elements of a sensor. FIG. 7 is a cross-sectional view of an alternate embodiment of a sensor 10E with a light diffracting material 100 disposed as a thin layer on a tissue-contacting surface 102 of the sensor body 104 applied to a patient's digit 106. The light diffracting material 100 is disposed in a region between an emitter 108 and a detector 110. Light shunted by the emitter 108, depicted by wavy arrow 112, impinges the light diffracting material 100. The light diffracting material reduces the reflectivity of the shunted light by "smearing" the light into multiple component wavelengths 114, many of which may interfere. The shunted light is thus prevented from reflecting around the gap between the sensor body 104 and the digit 106 to impinge the detector 110. It is contemplated that the diffracting material as described here and in FIG. 5D may be customized to selectively reduce certain wavelengths. Specifically, the slit pattern of diffraction grating may be optimized.

It should be appreciated that sensors as described herein may include light absorbing materials, light refracting materials, light diffracting materials, or any combination thereof. For example, a tissue-contacting surface, including all or part of any patterned regions or protruding features as described above, of a sensor body may be formed from, coated with, or impregnated with such materials. It should also be appreciated that, as discussed above, the sensor body may contain such materials only on a tissue-contacting surface, or, in alternate embodiments, the sensor body may be constructed entirely from such materials in appropriate regions as described herein.

It should also be appreciated that light absorbing materials may be adapted to absorb light at a particular wavelength. In certain embodiments, when light absorbing material is disposed between an emitter and a detector of a sensor, it may be advantageous to use light absorbing material that absorbs a wavelength emitted by the emitter in order to absorb shunted light from the emitter. For example, a light absorbing material may absorb at least about 50% of one or more wavelengths of light from the emitter, or may absorb a range of 50% to 95% of one or more wavelengths of light from the emitter. A light absorbing material may also absorb at least about 90% to at least 95% of one or more wavelengths of visible light and near-infrared light. In a specific embodiment, a pulse oximetry sensor may emit at least one wavelength of light in the wavelength range of 500 nm-1000 nm. For example, a sensor may emit light and wavelengths of 660 nm and 900 nm, which are wavelengths that may be absorbed by dark pigment. In other embodiments, when the light absorbing material is disposed near the edges of a sensor in order to absorb ambient light, which includes multiple wavelengths of light, it may be desirable to use an absorptive material that is adapted to absorb a broad range of wavelengths. Examples of light absorbing materials may include, but are not limited to, black or dark pigment, black or dark woven fabric or cloth, and infrared blockers.

Keeping in mind the preceding points, the exemplary sensor designs herein are provided as examples of sensors that increase the amount of light collected by a sensor 10 that has passed through perfused tissue while reducing or eliminating outside light and/or shunted light. It should be appreciated that a sensor 10 according to the present teachings may be adapted for use on any digit, and may also be adapted for use on a forehead, earlobe, or other sensor site. For example, a sensor 10 may be a clip-style sensor, appropriate for a patient earlobe or digit. Alternatively, a sensor 10 may be a bandage-style or wrap-style sensor for use on a digit or forehead.

Figure 8:
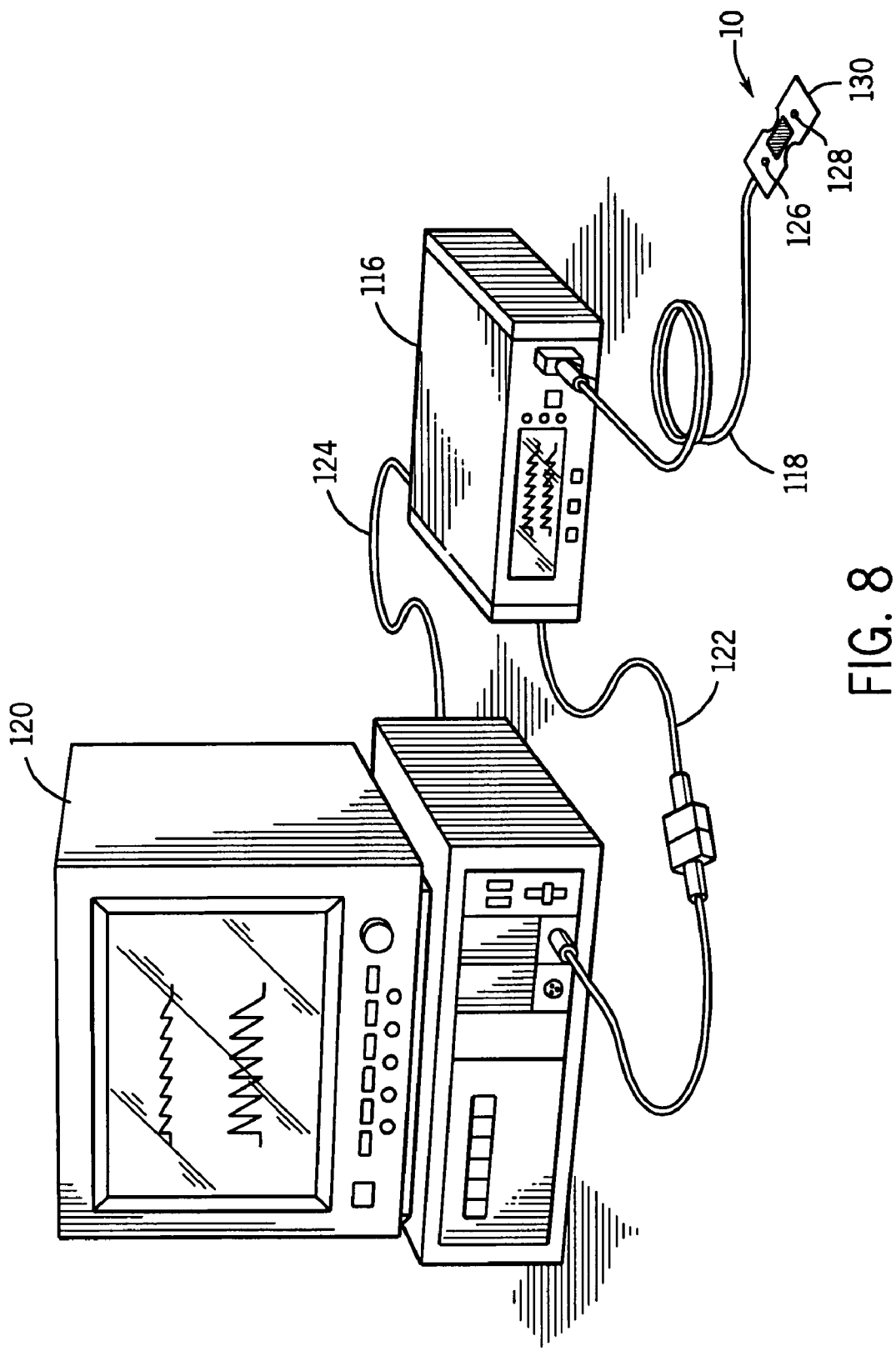
FIG. 8 illustrates a pulse oximetry system coupled to a multi-parameter patient monitor and a sensor according to embodiments of the present invention.

A sensor, illustrated generically as a sensor 10, may be used in conjunction with a pulse oximetry monitor 116, as illustrated in FIG. 8. It should be appreciated that the cable 118 of the sensor 10 may be coupled to the monitor 116 or it may be coupled to a transmission device (not shown) to facilitate wireless transmission between the sensor 10 and the monitor 116. The monitor 116 may be any suitable pulse oximeter, such as those available from Nellcor Puritan Bennett Inc. Furthermore, to upgrade conventional pulse oximetry provided by the monitor 116 to provide additional functions, the monitor 116 may be coupled to a multi-parameter patient monitor 120 via a cable 122 connected to a sensor input port or via a cable 124 connected to a digital communication port.

The sensor 10 includes an emitter 126 and a detector 128 that may be of any suitable type. For example, the emitter 126 may be one or more light emitting diodes adapted to transmit one or more wavelengths of light in the red to infrared range, and the detector 128 may be a photodetector selected to receive light in the range or ranges emitted from the emitter 126. For pulse oximetry applications using either transmission or reflectance type sensors the oxygen saturation of the patient's arterial blood may be determined using two or more wavelengths of light, most commonly red and near infrared wavelengths. Similarly, in other applications, a tissue water fraction (or other body fluid related metric) or a concentration of one or more biochemical components in an aqueous environment may be measured using two or more wavelengths of light, most commonly near infrared wavelengths between about 1,000 nm to about 2,500 nm. It should be understood that, as used herein, the term "light" may refer to one or more of infrared, visible, ultraviolet, or even X-ray electromagnetic radiation, and may also include any wavelength within the infrared, visible, ultraviolet, or X-ray spectra.

The emitter 126 and the detector 128 may be disposed on a sensor body 130, which may be made of any suitable material, such as plastic, rubber, silicone, foam, woven material, or paper. Alternatively, the emitter 126 and the detector 128 may be remotely located and optically coupled to the sensor 10 using optical fibers. In the depicted embodiments, the sensor 10 is coupled to a cable 118 that is responsible for transmitting electrical and/or optical signals to and from the emitter 126 and detector 128 of the sensor 10. The cable 118 may be permanently coupled to the sensor 10, or it may be removably coupled to the sensor 10—the latter alternative being more useful and cost efficient in situations where the sensor 10 is disposable.

The sensor 10 may be a "transmission type" sensor. Transmission type sensors include an emitter 126 and detector 128 that are typically placed on opposing sides of the sensor site. If the sensor site is a fingertip, for example, the sensor 10 is positioned over the patient's fingertip such that the emitter 126 and detector 128 lie on either side of the patient's nail bed. In other words, the sensor 10 is positioned so that the emitter 126 is located on the patient's fingernail and the detector 128 is located 180° opposite the emitter 126 on the patient's finger pad. During operation, the emitter 126 shines one or more wavelengths of light through the patient's fingertip and the light received by the detector 128 is processed to determine various physiological characteristics of the patient. In each of the embodiments discussed herein, it should be understood that the locations of the emitter 126 and the detector 128 may be exchanged. For example, the detector 128 may be located at the top of the finger and the emitter 126 may be located underneath the finger. In either arrangement, the sensor 10 will perform in substantially the same manner.

Reflectance type sensors generally operate under the same general principles as transmittance type sensors. However, reflectance type sensors include an emitter 126 and detector 128 that are typically placed on the same side of the sensor site. For example, a reflectance type sensor may be placed on a patient's fingertip or forehead such that the emitter 126 and detector 128 lie side-by-side. Reflectance type sensors detect light photons that are scattered back to the detector 128.

While the invention may be susceptible to various modifications and alternative forms, specific embodiments have been shown by way of example in the drawings and have been described in detail herein. However, it should be understood that the invention is not intended to be limited to the particular forms disclosed. Indeed, the present techniques may not only be applied to measurements of blood oxygen saturation, but these techniques may also be utilized for the measurement and/or analysis of other blood constituents using principles of pulse oximetry. For example, using the same, different, or additional wavelengths, the present techniques may be utilized for the measurement and/or analysis of carboxyhemoglobin, met-hemoglobin, total hemoglobin, intravascular dyes, and/or water content. Rather, the invention is to cover all modifications, equivalents, and alternatives falling within the spirit and scope of the invention as defined by the following appended claims.

What is claimed is:

1. A sensor comprising:
   a sensor body adapted to operate in a transmission mode;
   an emitter disposed on the sensor body, wherein the emitter is adapted to deliver a first light into a tissue;
   a detector disposed on the sensor body, wherein the detector is adapted to detect the first light; and
   at least one protrusion comprising a surface protruding non-orthogonally from a tissue-contacting surface of the sensor body and comprising a patterned region disposed on a surface of the protrusion, and wherein the at least one protrusion is adapted to reduce the amount of a second light impinging the detector at an incident angle substantially not in-line with an imaginary axis connecting the emitter and the detector.

2. The sensor, as set forth in claim 1, wherein the sensor comprises at least one of a pulse oximetry sensor or a sensor for measuring a water fraction.

3. The sensor, as set forth in claim 1, wherein the emitter comprises at least one light emitting diode.

4. The sensor, as set forth in claim 1, wherein the detector comprises at least one photodetector.

5. The sensor, as set forth in claim 1, wherein the at least one protrusion protrudes less than about 0.001 mm from the tissue-contacting surface.

6. The sensor, as set forth in claim 1, wherein the at least one protrusion comprises multiple protrusions.

7. The sensor, as set forth in claim 1, wherein the at least one protrusion comprises a light absorbing material.

8. The sensor, as set forth in claim 1, wherein the patterned region comprises a checker board pattern, a striped pattern, or a concentric circles pattern.

9. The sensor, as set forth in claim 1, wherein the patterned region comprises alternating regions of a first material and a second material.

10. The sensor, as set forth in claim 1, wherein the patterned region comprises a material applied in varying intensity or concentration to the protrusion.

11. A pulse oximetry system comprising:
    a pulse oximetry monitor; and
    a pulse oximetry sensor adapted to be operatively coupled to the monitor, the sensor comprising:
      a sensor body adapted to operate in transmission mode;
      an emitter disposed on the sensor body, wherein the emitter is adapted to deliver a first light into a tissue;
      a detector disposed on the sensor body, wherein the detector is adapted to detect the first light; and
      at least one protrusion comprising a surface protruding non-orthogonally from a tissue-contacting surface of the sensor body, wherein the at least one protrusion comprises a patterned region disposed on the surface of the protrusion, wherein the at least one protrusion is adapted to reduce the amount of a second light impinging the detector at an incident angle substantially not in-line with an imaginary axis connecting the emitter and the detector.

12. The pulse oximetry system, as set forth in claim 11, wherein the sensor comprises a sensor for measuring a water fraction.

13. The pulse oximetry system, as set forth in claim 11, wherein the emitter comprises at least one light emitting diode.

14. The pulse oximetry system, as set forth in claim 11, wherein the detector comprises at least one photodetector.

15. The pulse oximetry system, as set forth in claim 11, wherein the at least one protrusion protrudes less than about 0.001 mm from the tissue-contacting surface.

16. The pulse oximetry system, as set forth in claim 11, wherein the at least one protrusion comprises multiple protrusions.

17. The pulse oximetry system, as set forth in claim 11, wherein the at least one protrusion comprises a light absorbing material.

18. The system, as set forth in claim 11, wherein the patterned region comprises a checker board pattern, a striped pattern, or a concentric circles pattern.

19. The system, as set forth in claim 11, wherein the patterned region comprises alternating regions of a first material and a second material.

20. The system, as set forth in claim 11, wherein the at least one protrusion is situated along an edge of the sensor body.

21. The system, as set forth in claim 11, wherein the at least one protrusion substantially surrounds the emitter or the detector.

22. A method comprising:
    delivering a first light through a patient's tissue with a sensor adapted to operate in transmission mode;
    detecting the first light delivered through the tissue; and
    redirecting a second light that does not propagate through the tissue away from the detector with a protruding feature comprising a patterned region disposed on a surface of the protruding feature, wherein the surface of the protruding feature protrudes non-orthogonally from a tissue-contacting surface of the sensor body.

23. The method, as set forth in claim 22, wherein redirecting the second light comprises absorbing the second light.

24. The method, as set forth in claim 22, wherein redirecting the second light comprises destructively interfering with at least one wavelength of the second light.

25. A method comprising:
providing a transmission-type sensor body;
providing an emitter adapted to transmit a first light into tissue;
providing a detector adapted to detect the first light;
providing at least one protrusion disposed on a tissue-contacting surface of the sensor body, wherein the at least one protrusion comprises a patterned region disposed on a surface of the protrusion, and wherein the at least one protrusion comprises a light diffracting material capable of destructively interfering with at least one wavelength of a second light impinging the detector at an incident angle substantially not in-line with an imaginary axis connecting the emitter and the detector.

26. The method, as set forth in claim 25, wherein the at least one protrusion comprises a light absorbing material.

27. The method, as set forth in claim 25, wherein the at least one protrusion substantially surrounds the emitter or the detector.

28. A sensor comprising:
a sensor body adapted to operate in a transmission mode;
an emitter disposed on the sensor body, wherein the emitter is adapted to deliver a first light into a tissue;
a detector disposed on the sensor body, wherein the detector is adapted to detect the first light; and
at least one protrusion comprising a patterned region disposed on a surface of the protrusion, wherein the at least one protrusion is disposed on a tissue-contacting surface of the sensor body, and wherein the at least one protrusion comprises a light diffracting material, wherein the light diffracting material is adapted to destructively interfere with a wavelength of light emitted by the emitter.

29. The sensor, as set forth in claim 28, wherein the light diffracting material comprises an interference grating material.

30. A pulse oximetry system comprising:
a pulse oximetry monitor; and
a pulse oximetry sensor adapted to be operatively coupled to the monitor, the sensor comprising:
a sensor body adapted to operate in transmission mode;
an emitter disposed on the sensor body, wherein the emitter is adapted to deliver a first light into a tissue;
a detector disposed on the sensor body, wherein the detector is adapted to detect the first light; and
at least one protrusion comprising a patterned region disposed on a surface of the protrusion, wherein the at least one protrusion is disposed on a tissue-contacting surface of the sensor body, and wherein the at least one protrusion comprises a light diffracting material, wherein the light diffracting material is adapted to destructively interfere with a wavelength of light emitted by the emitter.

31. The pulse oximetry system, as set forth in claim 30, wherein the light diffracting material comprises an interference grating material.

* * * * *